(12) United States Patent
Roh et al.

(10) Patent No.: US 12,245,835 B2
(45) Date of Patent: Mar. 11, 2025

(54) REAL-TIME ADJUSTMENT OF HAPTIC FEEDBACK IN SURGICAL ROBOTS

(71) Applicant: IX Innovation LLC, Seattle, WA (US)

(72) Inventors: Jeffrey Roh, Seattle, WA (US); Justin Esterberg, Mesa, AZ (US); John Cronin, Jericho, VT (US); Seth Cronin, Essex Junction, VT (US); Michael D'Andrea, Burlington, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 18/377,686

(22) Filed: Oct. 6, 2023

(65) Prior Publication Data

US 2024/0033028 A1    Feb. 1, 2024

Related U.S. Application Data

(63) Continuation of application No. 17/407,538, filed on Aug. 20, 2021, now Pat. No. 11,779,423.

(51) Int. Cl.
*A61B 34/10* (2016.01)
*A61B 34/00* (2016.01)
(Continued)

(52) U.S. Cl.
CPC ............ *A61B 34/76* (2016.02); *A61B 34/10* (2016.02); *A61B 34/37* (2016.02); *A61B 90/361* (2016.02);
(Continued)

(58) Field of Classification Search
CPC .......... A61B 18/1492; A61B 2090/065; A61B 5/6852; A61B 2018/00351; A61B 2018/00577; A61B 2018/00839; A61B 2018/1467; A61B 34/20; A61B 5/6885; A61B 90/06; A61B 18/1206; A61B 2017/00026; A61B 2017/00477; A61B 2018/00029; A61B 2018/00357; A61B 2018/00642; A61B 2018/00648; A61B 2018/00875; A61B 2018/1465; A61B 2034/2055; A61B 2034/301;
(Continued)

(56) References Cited

U.S. PATENT DOCUMENTS

2012/0158011 A1   6/2012   Sandhu et al.
2017/0354470 A1   12/2017   Farritor et al.
(Continued)

*Primary Examiner* — Scott Luan
(74) *Attorney, Agent, or Firm* — Fish & Richardson P.C.

(57) ABSTRACT

Haptic feedback from a robotic surgical tool can be adjusted based on intra-operative assessment of the accuracy of a pre-operative surgical navigational plans. Navigational reference points are identified in at least one pre-operative image. At least one haptic response is identified for interactions between at least one robotic surgical tool and at least one navigational reference point. At least one intra-operative image is compared to the pre-operative image to determine the relative position of at least two corresponding navigational reference points in the images. The reference points' relative position determines a confidence level in the accuracy of the pre-operative navigational reference point. The haptic response is adjusted in timing, location, type, or amplitude based upon the confidence level. Tolerances and surgical navigation plan may also be updated and altered based on the confidence level.

20 Claims, 9 Drawing Sheets

(51) Int. Cl.
    *A61B 34/37*     (2016.01)
    *A61B 90/00*     (2016.01)
    *A61B 34/20*     (2016.01)
(52) U.S. Cl.
    CPC ........ *A61B 90/37* (2016.02); *A61B 2034/107* (2016.02); *A61B 2034/2065* (2016.02); *A61B 2034/742* (2016.02); *A61B 2034/744* (2016.02); *A61B 2090/364* (2016.02)
(58) Field of Classification Search
    CPC ........ A61B 2034/305; A61B 2034/741; A61B 2034/742; A61B 2090/064; A61B 2218/002; A61B 34/30; A61B 34/37; A61B 34/71; A61B 34/76; A61B 34/77; A61B 5/6843; A61B 2034/2051; A61B 2562/043; A61B 5/063; A61B 5/4839; A61B 5/74
    See application file for complete search history.

(56) References Cited

U.S. PATENT DOCUMENTS

| | | |
|---|---|---|
| 2019/0117111 A1 | 4/2019 | Osadchy et al. |
| 2020/0078097 A1 | 3/2020 | Gregerson et al. |
| 2021/0196425 A1 | 7/2021 | Shelton |

REAL-TIME ADJUSTMENT OF HAPTIC FEEDBACK IN SURGICAL ROBOTS

CROSS-REFERENCE TO RELATED APPLICATIONS

This application is a continuation of U.S. application Ser. No. 17/407,538, filed on Aug. 20, 2021, the entire contents of which are hereby incorporated by reference in their entirety.

FIELD OF THE DISCLOSURE

The present disclosure is generally related to systems and methods for improving context-specific feedback to surgeons during surgical procedures using robotic surgical equipment.

BACKGROUND

Advanced surgical systems include many different types of equipment to monitor and anesthetize the patient, assist the surgeon in performing surgical tasks, and maintain the environment of the operating room. Non-limiting examples of surgical equipment that may be used or improved by the present invention are provided for reference.

Vital signs monitor refers to medical diagnostic instruments and in particular to a portable, battery powered, multi-parametric, vital signs monitoring device that can be used for both ambulatory and transport applications as well as bedside monitoring. These devices can be used with an isolated data link to an interconnected portable computer allowing snapshot and trended data from the monitoring device to be printed automatically and also allowing default configuration settings to be downloaded to the monitoring device. The monitoring device is capable of use as a stand-alone unit as well as part of a bi-directional wireless communications network that includes at least one remote monitoring station. A number of vital signs monitoring devices are known that are capable of measuring multiple physiologic parameters of a patient wherein various sensor output signals are transmitted either wirelessly or by means of a wired connection to at least one remote site, such as a central monitoring station. A vital signs monitor can be integrated into the embodiments in a variety of manners.

Heart rate monitor refers to the sensor(s) and/or sensor system(s) that can be applied in the context of monitoring heart rates. Embodiments are intended to measure, directly or indirectly, any physiological condition from which any relevant aspect of heart rate can be gleaned. For example, some of the embodiments measure different or overlapping physiological conditions to measure the same aspect of heart rate. Alternatively, some embodiments measure the same, different, or overlapping physiological conditions to measure different aspects of heart rate, i.e., number of beats, strength of beats, regularity of beats, beat anomalies, etc. A heart rate monitor can be integrated into the embodiments in a variety of manners.

Pulse oximeter or SpO2 Monitor refers to a plethysmograph or any instrument that measures variations in the size of an organ or body part on the basis of the amount of blood passing through or present in the part. An oximeter is a type of plethysmograph that determines the oxygen saturation of the blood. One common type of oximeter is a pulse oximeter. A pulse oximeter is a medical device that indirectly measures the oxygen saturation of a patient's blood (as opposed to measuring oxygen saturation directly through a blood sample) and changes in blood volume in the skin. A pulse oximeter may include a light sensor that is placed at a site on a patient, usually a fingertip, toe, forehead, or earlobe, or in the case of a neonate, across a foot. Light, which may be produced by a light source integrated into the pulse oximeter, containing both red and infrared wavelengths is directed onto the skin of the patient and the light that passes through the skin is detected by the sensor. The intensity of light in each wavelength is measured by the sensor over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation. A pulse oximeter can be integrated into the embodiments in a variety of manners.

End Tidal CO2 monitor or capnography monitor refers to an instrument which is used for measurement of level of carbon dioxide (referred to as end tidal carbon dioxide, ETCO2) that is released at the end of an exhaled breath. End Tidal CO2 monitor or capnography monitor is widely used in anesthesia and intensive care. ETCO2 can be calculated by plotting expiratory CO2 with time. Further, ETCO2 monitor plays a very crucial role for the measurement of applications such as Cardiopulmonary Resuscitation (CPR), Airway assessment, Procedural sedation and analgesia, Pulmonary diseases such as obstructive pulmonary disease, pulmonary embolism, etc., heart failure, metabolic disorders, etc. The instrument can be configured as side stream (diverting) or mainstream (non-diverting). Diverting device transports a portion of a patient's respired gases from the sampling site to the sensor while non-diverting device does not transport gas away. Also, measurement by the instrument is based on the absorption of infrared light by carbon dioxide; where exhaled gas passes through a sampling chamber containing an infrared light source and photodetector on both sides. Based on the amount of infrared light reaching the photodetector, the amount of carbon dioxide present in the gas can be calculated. An ETCO2 monitor or capnography monitor can be integrated into the embodiments in a variety of manners.

Blood pressure monitor refers to any instrument that measures blood pressure, particularly in arteries. Blood pressure monitors use a non-invasive technique (by external cuff application) or an invasive technique (by a cannula needle inserted in artery, used in operating theatre) for measurement, with non-invasive measurement being widely used. The non-invasive method (referred to as sphygmomanometer further) works by measurement of force exerted against arterial walls during ventricular systole (i.e., systolic blood pressure, occurs when heart beats and pushes blood through the arteries) and ventricular diastole (i.e., diastolic blood pressure, occurs when heart rests and is filling with blood) thereby measuring systole and diastole, respectively. It can be of three types automatic/digital, manual (aneroid-dial), and manual (mercury-column). The sphygmomanometer may include a bladder, a cuff, a pressure meter, a stethoscope, a valve, and a bulb. After the cuff is placed around a patient's arm, the cuff then inflates until it fits tightly around the arm, cutting off the flow of blood, and then the valve opens to deflate the cuff. As the cuff is inflated tightly around the arm, the cuff pressure reaches the systolic pressure and blood begins to flow around the artery, creating a vibration which is detected by the meter and recorded as the systolic pressure. The techniques used for measurement may be either of auscultatory or oscillometric. A blood pressure monitor can be integrated into the embodiments in a variety of manners.

Body temperature monitor refers to any instrument which is used for measurement of body temperature. The instrument can measure the temperature invasively or non-invasively by placement of sensor into organs such as bladder, rectum, esophagus, tympanum, esophagus, etc., and mouth, rectum, armpit, etc., respectively. The sensors are of two types including contact and non-contact. Body temperature can be measured in two forms including core temperature and peripheral temperature. Temperature measurement can be done by sensing technologies such as thermocouples, resistive temperature devices (RTDs, thermistors), infrared radiators, bimetallic devices, liquid expansion devices, molecular change-of-state, and silicon diodes. A thermometer which is a commonly used instrument for the measurement of temperature consists of a temperature sensing element (e.g., temperature sensor) and a means for converting to a numerical value. A blood temperature monitor can be integrated into the embodiments in a variety of manners.

Respiration rate or breathing rate is the rate at which breathing occurs and is measured by counting the number of breaths a person takes per minute. The rate is usually measured when a person is at rest and simply involves counting the number of breaths for one minute by counting how many times the chest rises. Normal respiration rates for an adult person at rest are in the range of 12 to 16 breaths per minute. A variation can be an indication of an abnormality/medical condition or a patient's demographic parameters. Hypoxia is a condition with low levels of oxygen in the cells and hypercapnia is a condition in which high levels of carbon dioxide in the bloodstream. Pulmonary disorders, asthma, anxiety, pneumonia, heart diseases, dehydration, drug overdose are some of the abnormal conditions which can bring a change to the respiration rate, thereby increasing or reducing the respiration rate from normal levels. Respiratory rate can be integrated into the embodiments in a variety of manners.

An electrocardiogram abbreviated as EKG or ECG refers to a representation of the electrical activity of the heart (graphical trace of voltage versus time) which is done by placement of electrodes on skin/body surface. The electrodes capture the electrical impulse which travels through the heart causing systole and diastole or the pumping of the heart. This impulse gives a lot of information related to the normal functioning of the heart and the production of impulses. A change may occur due to medical conditions such as arrhythmias (tachycardia where the heart rate becomes faster and bradycardia where the heart rate becomes slower), coronary heart disease, heart attacks, cardiomyopathy. The instrument used for the measurement of the electrocardiogram is called an electrocardiograph which measures the electrical impulses by the placement of electrodes on the surface of the body and represents the ECG by a PQRST waveform. PQRST wave is read as: P wave which represents the depolarization of the left and right atrium and corresponding to atrial contraction, QRS complex indicates ventricular depolarization and represents the electrical impulse as it spreads through the ventricles; T wave indicates ventricular repolarization and follows the QRS complex. An electrocardiogram can be integrated into the embodiments in a variety of manners.

Neuromonitoring also called Intraoperative neurophysiological monitoring (abbreviated as IONM) refers to an assessment of functions and changes in the brain, brainstem, spinal cord, cranial nerves, and peripheral nerves during a surgical procedure on these organs. It includes both continuous monitoring of neural tissue as well as the localization of vital neural structures. IONM measures changes in these organs which are indicative of irreversible damage, injuries in the organs, aiming at reducing the risk of neurological deficits after operations involving the nervous system. This has also been found to be effective in localization of anatomical structures, including peripheral nerves and sensorimotor cortex, which help in guiding the surgeon during dissection. Electrophysiological modalities which are employed in neuromonitoring are an extracellular single unit and local field recordings (LFP), Somatosensory Evoked Potential (SSEP), transcranial electrical motor evoked potentials (TCeMEP), Electromyography (EMG), electroencephalography (EEG), and auditory brainstem response (ABR). The use of neurophysiological monitoring during surgical procedures requires specific anesthesia techniques to avoid interference and signal alteration due to anesthesia. Neuromonitoring can be integrated into the embodiments in a variety of manners.

Motor Evoked Potential abbreviated as MEP refers to electrical signals which are recorded from descending motor pathways or muscles following stimulation of motor pathways within the brain. MEP may be calculated by measurement of the action potential which is elicited by non-invasive stimulation of the motor cortex through the scalp. MEP is a widely used technique for intraoperative monitoring and neurophysiological testing of the motor pathways specifically during spinal procedures. The technique of monitoring for measurement of MEP can be defined based on some of the parameters like a site of stimulation (motor cortex or spinal cord), method of stimulation (electrical potential or magnetic field), and site of recording (spinal cord or peripheral mixed nerve and muscle). The target site may be stimulated by the use of electrical or magnetic means. MEP can be integrated into the embodiments in a variety of manners.

Somatosensory evoked potential abbreviated as SSEP or SEP refers to the electrical signals which are elicited by the brain and the spinal cord in response to sensory stimulus or touch. SSEP is one of the most frequently used techniques for intraoperative neurophysiological monitoring in spinal surgeries. The method proves to be very reliable which allows for continuous monitoring during a surgical procedure. However, accuracy may be a concern at times in measurement. The sensor stimulus which is commonly given to the organs may be auditory, visual, or somatosensory SEPs and applied on the skin, peripheral nerves of the upper limb, lower limb, or scalp. The stimulation technique may be mechanical (widely used), or electrical (found to give larger and more robust responses), intraoperative spinal monitoring modality. Somatosensory evoked potential can be integrated into the embodiments in a variety of manners.

Electromyography abbreviated as EMG refers to the evaluation and recording of electrical signals or electrical activity of the skeletal muscles. Electromyography instrument or Electromyograph or Electromyogram, the instrument for the measurement of the EMG activity works on a technique used for a recording of electrical activity produced by skeletal muscles and evaluation of the functional integrity of individual nerves. The nerves which are monitored by the EMG instrument may be intracranial, spinal, or peripheral nerves. The electrodes which may be used for the acquisition of signals may be invasive and non-invasive electrodes. The technique used for measurement may be spontaneous or triggered. Spontaneous EMG refers to the recording of myoelectric signals during surgical manipulation such as compression, stretching, or pulling of nerves produces; and does not perform external stimulation. Spontaneous EMG may be recorded by the insertion of a needle electrode. Triggered EMG refers to the recording of myoelectric signals during stimulation of target site such as pedicle screw with incremental current intensities. Electromyography can be integrated into the embodiments in a variety of manners.

Electroencephalography abbreviated as EEG refers to the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp where each pair of electrodes transmit a signal to one or more recording channels. It is one of the oldest and most commonly utilized modalities for intraoperative neurophysiological monitoring and assessing cortical perfusion and oxygenation during a variety of vascular, cardiac, and neurosurgical procedures. The waves produced by EEG are Alpha, Beta, Theta, and Delta. Electroencephalography can be integrated into the embodiments in a variety of manners.

Medical visualization systems refer to visualization systems that are used for visualization and analysis of objects (preferably three-dimensional (3D) objects). Medical visualization systems include the selection of points at surfaces, selection of a region of interest, selection of objects. Medical visualization systems may be used for applications diagnosis, treatment planning, intraoperative support, documentation, educational purpose. Medical visualization systems may consist of microscopes, endoscopes/arthroscopes/laparoscopes, fiber optics, surgical lights, high-definition monitors, operating room cameras, etc. 3D visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times. Medical visualization systems can be integrated into the embodiments in a variety of manners.

A microscope refers to an instrument that is used for viewing samples and objects that cannot be seen with an unaided eye. A microscope may have components eyepiece, objective lenses, adjustment knobs, a stage, an illuminator, a condenser, and a diaphragm. A microscope works by manipulating how light enters the eye using a convex lens, where both sides of the lens are curved outwards. When light reflects off of an object being viewed under the microscope and passes through the lens, it bends towards the eye. This makes the object look bigger than it is. Microscope may be of a variety of types including compound (light illuminated and the image seen with the microscope is two dimensional), dissection or stereoscope (light illuminated and image seen with the microscope is three dimensional), confocal (laser-illuminated and image seen with the microscope on a digital computer screen), Scanning Electron abbreviated as SEM (electron illuminated and image seen with the microscope in black and white), and Transmission Electron Microscope abbreviated as TEM (electron illuminated and image seen with the microscope is the high magnification and high resolution). A microscope can be integrated into the embodiments in a variety of manners.

Endoscopes or arthroscopes or laparoscopes refer to minimally invasive surgical techniques where procedures are performed by performing minimal incision in the body. An endoscope refers to an instrument to visualize, diagnose, and treat problems inside hollow organs where the instrument is inserted through natural body openings such as the mouth or anus. An endoscope may perform a procedure by inserting a scope with a tiny camera attached to a long, thin tube into a natural body orifice. The doctor moves it through a body passageway or opening to see inside an organ. It can be used for diagnosis and surgery (such as for removing polyps from the colon). Arthroscope refers to an instrument to visualize, diagnose, and treat problems inside a joint by a TV camera inserted through small portals/incisions and to perform procedures on cartilage, ligaments, tendons, etc. An arthroscope may perform the procedure as follows: a surgeon makes a small incision in a patient's skin and inserts a pencil-sized instrument with a small lens and lighting system to magnify the target site (joint) and viewing of the interior of the joint by means of a miniature television camera and performing procedure. Laparoscope refers to an instrument to visualize, diagnose, and treat problems inside soft organs like the abdomen and pelvis by a TV camera inserted through small portals/incisions and to perform procedures. Endoscopes/arthroscopes/laparoscopes or minimally invasive surgery techniques can be integrated into the embodiments in a variety of manners.

Fiber optics refers to flexible, transparent fiber made by drawing glass (silica) or plastic to a diameter slightly thicker than that of a human hair. Fiber optics are arranged in bundles called optical cables and used to transmit light signals over long distances. Fiber optics are used most often as a means to transmit light between the two ends of the fiber and find wide usage in the medical field. Traditional surgery requires sizable and invasive incisions to expose internal organs and operate on affected areas and with fiber optics much smaller surgical incisions can be performed. Fiber optics contain components core, cladding, buffer coating. Fiber optics may be inserted in hypodermic needles and catheters, endoscope, operation theatres, ophthalmology, dentistry tools. Fiber optic sensors comprise a light source, optical fiber, external transducer, and photodetector. Fiber optic sensors may be intrinsic or extrinsic. Fiber optic sensors may be categorized into four types physical, imaging, chemical, and biological. Fiber optics can be integrated into the embodiments in a variety of manners.

Surgical lights also referred to as operating light refers to an instrument that performs illumination of a local area or cavity of the patient. Surgical lights play an important role in illumination before, during, and after a medical procedure. Surgical lights may be categorized by lamp type as conventional (incandescent) and LED (light-emitting diode). Surgical lights may be categorized by mounting configuration as ceiling-mounted, wall-mounted, or floor stand. Surgical lights may be categorized by type as tungsten, quartz, and/or xenon halogens and light-emitting diodes (LEDs). Surgical lights include sterilizable handles which allow the surgeon to adjust light positions. Some important factors affecting surgical lights may be illumination, shadow management (cast shadows and contour shadows), the volume of light, heat management, fail-safe surgical lighting. Surgical lights can be integrated into the embodiments in a variety of manners.

High definition monitors refer to a display in which a clearer picture than possible with low-definition, low-resolution screens. High-definition monitors have a higher density of pixels per inch than past standard TV screens.

Resolution for high definition monitors may be 1280×720 pixels or more. Full High-Definition (HD) monitors may be 1920×1080 pixels, Quad HD monitors may be 2560×1440 pixels, 4K monitors may be 3840×2160 pixels, 8K monitors may be 7680×4320 pixels. High definition monitors may operate in progressive or interlaced scanning mode. High definition monitors used in medical applications may offer the following advantages improved visibility and allows for precise and safe surgery, rich color reproduction and provides suitable colors for each clinical discipline, better visibility, and operability with a large screen and electronic zoom, higher image quality in low light conditions, high contrast at high spatial frequencies, twice as sensitive as conventional sensors, easier determination of tissue boundaries (fat, nerves, vessels, etc.), and better visualization of blood vessels and lesions. High definition monitors can be integrated into the embodiments in a variety of manners.

Operating room cameras refer to cameras that collect images from 360 degrees, and sensors that monitor both the operating room and people in it. Operating room cameras consist of cameras that are equipped in system and perform recording to give a bird's-eye view to the surgical team. Some cameras are on devices that surgeons insert through small incisions or orifices to see what they are doing during minimally invasive surgery. Operating room cameras may perform recording for various purposes. Operating room cameras may perform recordings for educational purposes, for example. to broadcast a live feed of a surgical demonstration to a remote audience; to collect authentic footage for edited, instructional videos on a surgical technique or procedure; to facilitate video enhanced debriefing and coaching, or to formally assess surgical skills. Operating room cameras can be integrated into the embodiments in a variety of manners.

Surgical tower refers to an instrument used for performing minimally invasive surgery or surgery which is performed by creating small incisions in the body, therefore they are also referred to as minimally invasive devices or minimally invasive access devices. The procedure of performing minimally invasive surgery may be referred to as minimally invasive procedure or minimally invasive surgery, abbreviated as MIS. MIS is a safe, less invasive, and precise surgical procedure. Some of the advantages offered by surgical towers may be small incisions, less pain, low risk of infection, short hospital stays, quick recovery time, less scarring, and reduced blood loss. Some medical procedures where surgical towers are useful and are widely used may be lung procedures, gynecological, head and neck, heart, and urological conditions. MIS may be robotic or non-robotic/endoscopic. MIS may include the following: endoscopic, laparoscopic, arthroscopic, natural orifice intraluminal, and natural orifice transluminal procedures. A surgical tower access device may be designed as an outer sleeve and an inner sleeve that telescoping or slidably engages with one another. When a telescope is used to operate on the abdomen, the procedure is called laparoscopy. Surgical towers typically include access to a variety of surgical tools, such as, for example, electrocautery, radiofrequency, lasers, sensors, etc. A surgical tower can be integrated into the embodiments in a variety of manners.

Electrocautery refers to an instrument that is used for burning a part of the body to remove or close off a part of it. Various physiological conditions or surgical procedures require the removal of body tissues and organs, a consequence of which is bleeding. In order to achieve hemostasis and for removing and sealing all blood vessels which are supplied to an organ after surgical incision an electrocautery instrument may be used. For example, after removing part of the liver for removal of tumor etc., blood vessels in the liver must be sealed individually. An electrocautery instrument may be used for sealing living tissue such as arteries, veins, lymph nodes, nerves, fats, ligaments, and other soft tissue structures. It may be used in applications surgery, tumor removal, nasal treatment, wart removal. Electrocautery may operate in two modes including monopolar or bipolar. The electrocautery instrument may consist of a generator, a handpiece, and one or more electrodes. Electrocautery can be integrated into the embodiments in a variety of manners.

Radiofrequency (RF) is used in association with minimally invasive surgery devices. The radiofrequency (RF) may be used for the treatment of skin by delivering it to the skin through a minimally invasive tool (fine needles) which does not require skin excision. The RF may be used for real-time tracking of minimally invasive surgery devices such as laparoscopic instruments. The RF may provide radiofrequency ablation to a patient suffering from atrial fibrillation through smaller incisions made between the ribs. The RF may be used to perform an endoscopic surgery on the body such as the spine by delivery of RF energy. Radiofrequency can be integrated into the embodiments in a variety of manners.

Laser is used in association with minimally invasive surgery devices. The laser may be used in minimally invasive surgeries with an endoscope. The laser is attached to the distal end of the endoscope and steers the laser at high speed by producing higher incision quality than existing surgical tools and minimizing damage to surrounding tissue. Laser may be used to perform minimally invasive surgeries using an endoscope, laparoscope in the lower and upper gastrointestinal tract, eye, nose, and throat. Lasers are used in minimally invasive surgery to ablate soft tissues, such as a herniated spinal disc bulge. Laser can be integrated into the embodiments in a variety of manners.

Sensors are used in a variety of medical settings and in various procedures. Sensor may be electrical or optical, consisting of capacitive, inductive, piezoelectric, piezoresistive, magnetic, and auditory. The sensors may be used in robotic, laparoscopic, palpation, biopsy, heart ablation, and valvuloplasty. Sensors can be integrated into the embodiments in a variety of manners.

Imaging systems refer to techniques or instruments which are used for the creation of images and visualization of the interior of a human body for diagnostic and treatment purposes. Imaging systems play a crucial role in every medical setting and can help in the screening of health conditions, diagnosing causes of symptoms, monitor health conditions. Imaging systems may include various imaging techniques such as X-ray, Fluoroscopy, Magnetic resonance imaging (MRI), Ultrasound, Endoscopy, Elastography, Tactile imaging, Thermography, Medical photography, and Nuclear medicine e.g., Positron emission tomography (PET). Some factors which may drive the market are cost and clinical advantages of medical imaging modalities, a rising share of ageing populations, increasing prevalence of cardiovascular or lifestyle diseases, and increasing demand from emerging economies. Some factors which may inhibit the market are saturation in many segments, high costs, and lack of trained personnel. Imaging systems can be integrated into the embodiments in a variety of manners.

X-ray refers to a medical imaging instrument that uses X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of x-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type of tissue the X-rays pass through and their densities. Some of the applications where X-rays are used may be bone fractures, infections, calcification, tumors, arthritis, blood vessel blockages, digestive problems, heart problems. The X-ray instrument may consist of components such as an x-ray tube, an operating console, a collimator, grids, a detector, radiographic film, etc. An X-ray can be integrated into the embodiments in a variety of manners.

Magnetic resonance imaging abbreviated as MRI refers to a medical imaging instrument that uses powerful magnets for the creation of images of the interior of the human body for diagnostic and treatment purposes. Some of the applications where MRI may be used may be brain/spinal cord anomalies, tumors in the body, breast cancer screening, joint injuries, uterine/pelvic pain detection, and heart problems. For the creation of the image by an MRI instrument, magnetic resonance is produced by powerful magnets which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field, and energy release is dependent on environmental factors and the chemical nature of the molecules. MRI may more widely suit for imaging of non-bony parts or soft tissues of the body. MRI may be less harmful as it does not use damaging ionizing radiation as in the X-ray instrument. MRI instrument may consist of magnets, gradients, a radiofrequency system, and a computer control system. Some areas where imaging by MRI should be prohibited may be people with implants. MRI can be integrated into the embodiments in a variety of manners.

Computed tomography imaging abbreviated as CT refers to a medical imaging instrument that uses an X-ray radiation (i.e., X-ray range in the electromagnetic radiation spectrum) for the creation of cross-sectional images of the interior of the human body for diagnostic and treatment purposes. CT refers to a computerized x-ray imaging procedure in which a narrow beam of X-rays is aimed at a patient and quickly rotated around the body, producing signals that are processed by the machine's computer to generate cross-sectional images—or "slices"—of the body The CT instrument produces cross-sectional images of the body. Computed tomography instrument is different from an X-ray instrument as it creates 3-dimensional cross-sectional images of the body while X-ray creates 2-dimensional images of the body; the 3-dimensional cross-sectional images are created by taking images from different angles, which is done by taking a series of tomographic images from different angles. The different taken images are collected by a computer and digitally stacked to form a three-dimensional image of the patient. For creation of images by the CT instrument, a CT scanner uses a motorized X-ray source that rotates around the circular opening of a donut-shaped structure called a gantry while the X-ray tube rotates around the patient shooting narrow beams of X-rays through the body. Some of the applications where CT may be used may be blood clots and bone fractures, including subtle fractures not visible on X-ray, organ injuries. CT can be integrated into the embodiments in a variety of manners.

Stereotactic navigation systems refer to an instrument that uses patient imaging (e.g., CT, MRI) to guide surgeons in the placement of specialized surgical instruments and implants before and during a procedure. The patient images are taken to guide the physician before or during the medical procedure. The stereotactic navigation system includes a camera having infrared sensors to determine the location of the tip of the probe being used in the surgical procedure. This information is sent in real-time so that the surgeons have a clear image of the precise location of where they are working in the body. Stereotactic navigation systems may be framed (attachment of a frame to patient's head using screws or pins) or frameless (do not require the placement of a frame on the patient's anatomy). Stereotactic navigation systems may be used for diagnostic biopsies, tumor resection, bone preparation/implant placement, placement of electrodes, otolaryngologic, or neurosurgical procedures. Stereotactic navigation systems can be integrated into the embodiments in a variety of manners.

Ultrasound imaging also referred to as sonography or ultrasonography refers to a medical imaging instrument that uses ultrasound or sound waves (also referred to as acoustic waves) for the creation of cross-sectional images of the interior of the human body for diagnostic and treatment purposes. Ultrasound in the instrument may be produced by a piezoelectric transducer which produces sound waves and sends them into the body. The sound waves which are reflected are converted into electrical signals which are sent to an ultrasound scanner. Ultrasound instruments may be used for diagnostic and functional imaging. Ultrasound instruments may be used for therapeutic or interventional procedures. Some of the applications where ultrasound may be used are diagnosis, treatment, and guidance during medical procedures e.g., biopsies, internal organs such as liver, kidneys, or pancreas, fetal monitoring, etc., in soft tissues, muscles, blood vessels, tendons, and joints. Ultrasound may be used for internal (transducer is placed in organs e.g., vagina) and external (transducer is placed on chest for heart monitoring or abdomen for the fetus). An ultrasound machine may consist of a monitor, a keyboard, a processor, data storage, a probe, and a transducer. Ultrasound can be integrated into the embodiments in a variety of manners.

Anesthesiology machine refers to a machine that is used to generate and mix medical gases like oxygen or air and anesthetic agents to induce and maintain anesthesia in patients. Anesthesiology machines deliver oxygen and anesthetic gas to the patient as well as filter out expiratory carbon dioxide. Anesthesia machine may perform following functions provides O2, accurately mix anesthetic gases and vapors, enable patient ventilation, and minimize anesthesia related risks to patients and staff. Anesthesia machine may consist of the following essential components a source of oxygen (O2), an O2 flowmeter, a vaporizer (anesthetics include isoflurane, halothane, enflurane, desflurane, sevoflurane, and methoxyflurane), a patient breathing circuit (tubing, connectors, and valves), and a scavenging system (removes any excess anesthetics gases). Anesthesia machine may be divided into three parts the high pressure system, the intermediate pressure system, and the low-pressure system. The process of anesthesia starts with oxygen flow from pipeline or cylinder through the flowmeter, O2 flows through the vaporizer and picks up the anesthetic vapors, the O2-anesthetic mix then flows through the breathing circuit and into the patient's lungs, usually by spontaneous ventilation or normal respiration. The O2-anesthetic mix then flows through the breathing circuit and into the patient's lungs, usually by spontaneous ventilation or normal respiration. An anesthesiology machine can be integrated into the embodiments in a variety of manners.

Surgical bed is a bed equipped with mechanisms that can elevate or lower the entire bed platform, flex, or extend individual components of the platform, or raise or lower the head or the feet of the patient independently. Surgical bed may be an operation bed, cardiac bed, amputation bed, or fracture bed. Some essential components of a surgical bed may be a bed sheet, a woolen blanket, a bath towel, and a bed block. Surgical beds can also be referred to as a postoperative bed, refers to a special type of bed made for the patient who is coming from the operation theatre or from another procedure that requires anesthesia. The surgical bed is designed in a manner that makes it easier to transfer an unconscious or weak patient from a stretcher/wheelchair to the bed. The surgical bed should protect bed linen from vomiting, bleeding, drainage, and discharges, provide warmth and comfort to the patient to prevent shock, provide necessary position, which is suitable for operation, protect patient from being chilled, and prepared to meet any emergency. Surgical bed can be integrated into the embodiments in a variety of manners.

Disposable air warmer (also referred to as bair) refers to a convective temperature management system used in a hospital or surgery center to maintain a patient's core body temperature. The instrument consists of a reusable warming unit and a single-use disposable warming blankets for use during surgery and may also be used before and after surgery. The air warmer uses convective warming consisting of two components a warming unit and a disposable blanket. The air warmer filter air and then force warm air through disposable blankets which cover the patient. The blanket may be designed to use pressure points on the patient's body to prevent heat from reaching areas at risk for pressure sores or burns. The blanket may also include drain holes where fluid passes through the surface of the blanket to linen underneath which will reduce the risk of skin softening and reduce the risk of unintended cooling because of heat loss from evaporation. Disposable air warmer can be integrated into the embodiments in a variety of manners.

Sequential compression device abbreviated as SVD refers to an instrument that is used to help prevent blood clots in the deep veins of legs. The sequential compression device use cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using a DVT may be discomfort, warmth, or sweating beneath the cuff, skin breakdown, nerve damage, pressure injury. Sequential compression device can be integrated into the embodiments in a variety of manners.

Jackson frame (or Jackson table) refers to a frame or table which is designed for use in spine surgeries and may be used in a variety of spinal procedures in supine, prone, lateral positions in a safe manner. Two peculiar features of the Jackson table are no central table support and its ability to rotate the table through 180 degrees. The Jackson table is supported at both ends keeping the whole of the table free. This allows the visualization of trunk and major parts of extremities as well. The Jackson frame allows the patient to be slid from the cart onto the table in the supine position with appropriate padding placed. The patient is then strapped securely on the table. The Jackson frame can be integrated into the embodiments in a variety of manners.

Bed position controller refers to an instrument for controlling the position of the patient bed. Positioning a patient in bed is important for maintaining alignment and for preventing bed-sores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient may be in the following positions in a bed supine position, prone position, lateral position, sims position, fowler's position, semi-Fowler's position, orthopedic or tripod position, and Trendelenburg position. Bed position controller can be integrated into the embodiments in a variety of manners.

Operating room environmental controls refers to control or maintenance of the environment in an operation theatre where procedures are performed to minimize the risk of airborne infection and provide a conducive environment for everyone in the operation theatre including the surgeon, anesthesiologist, nurses and patient). Some factors which may contribute to poor quality in the environment of the operating room are temperature, ventilation, and humidity and they can lead to profound effects on the health of people in the operating room and work productivity. As an example: surgeons prefer a cool, dry climate since they work in bright, hot lights; anesthesia personnel prefer a warmer, less breezy climate; patient condition demands a relatively warm, humid, and quiet environment. Operating room environmental controls may control the environment by taking care of factors such as environmental humidity, infection, and odor control. Humidity control may be done by controlling the temperature of anesthesia gases, and infection can be controlled by the use of filters to purify the air. Operating room environmental controls can be integrated into the embodiments in a variety of manners.

Heating, ventilation, and air conditioning (abbreviated as HVAC) refers to a system for regulating environment of indoor settings by moving air between indoor and outdoor areas, along with heating and cooling. HVAC may use a different combination of systems, machines, and technologies to improve comfort. HVAC may be necessary to maintain the environment of an operating room. HVAC for an operating room may be a traditional operating room (which may have a large diffuser array directly above the operating table) or a hybrid operating room (which may have monitors and imaging equipment that consume valuable ceiling space and complicate the design process). HVAC may consist of three main units heating unit (it may be a furnace or a boiler), a ventilation unit (it may be natural or forced), and an air conditioning unit (which may remove existing heat). HVAC may be made of components as air return, filter, exhaust outlets, ducts, electrical elements, outdoor unit, compressor, coils, and blower. The HVAC system may use central heating and AC systems that use a single blower to circulate air via internal ducts. Heating, ventilation, and air conditioning can be integrated into the embodiments in a variety of manners.

Air purification refers to a system for removing contaminants from the air in a room to improve indoor air quality. Air purification may be important in an operating room as surgical site infection may be a reason for high mortality and morbidity. The air purification system may deliver clean, filtered, contaminant-free air over the operating room table with diffuser, airflow, etc., to remove all infectious particles down and away from the patient. Air purification system may be air curtain, multi-diffuser array, or single large diffuser (based on laminar diffuser flow) or High-Efficiency Particulate Air filter. High-Efficiency Particulate Air filter referred to as HEPA filter protects from infection and contamination by a filter which is mounted at the terminal of the duct. HEPA filter may be mounted on the ceiling and deliver clean, filtered air in a flow to the room that provides a sweeping effect that pushes contaminants out via the return grilles that are usually mounted on the lower wall. Air purification can be integrated into the embodiments in a variety of manners.

Orthopedic tools also referred to as orthopedic instruments used for treatment and prevention of deformities and injuries of musculoskeletal system or skeleton, articulations, and locomotive system (i.e., set formed by skeleton, muscles attached to it and part of nervous system which controls the muscles). Major percentage of orthopedic tools are made of plastic. Orthopedic tools may be divided into the following specialties hand and wrist, foot and ankle, shoulder and elbow, arthroscopy, hip, and knee. Orthopedic tool may be fixation tools, relieving tools, corrective tools, compression-distraction tools. Fixation tool refers to a tool designed to restrict movements partially or completely in a joint, e.g., hinged splints (for preserving a certain range of movement in a joint), rigid splints. Relieving tool refers to a tool designed to relieve pressure on an ailing part by transferring support to healthy parts of an extremity, e.g., Thomas splint and the Voskoboinikova apparatus. Corrective tool refers to a tool designed to gradually correct a deformity, e.g., corsets, splints, orthopedic footwear, and insoles and other devices to correct abnormal positions of the foot. Compression-distraction tool refers to a tool designed to correct acquired or congenital deformities of the extremities, e.g., curvature, shortening, and pseudarthrosis such as Gudushauri. Fixation tools may be internal fixation tools (e.g., screws, plates) or external fixation tools (radius, tibia fracture fixation). Orthopedic tools may be bone-holding forceps, drill bits, nail pins, hammer staple, etc. Orthopedic tools can be integrated into the embodiments in a variety of manners.

Drill refers to a tool for making holes in bones for insertion of implants like nails, plates, screws, and wires. The drill tool functions by drilling cylindrical tunnels into bone. Drill may be used in orthopedics for performing medical procedures. Use of drill on bones may have some risks of harm caused to the bone, muscle, nerves, and venous tissues if the drill does not stop immediately upon contact with an unintended surface. Drills vary widely in speed, power, and size. Drill may be powered as electrical, pneumatic, or battery. Drills generally may work on speed below 1000 rpm in orthopedic. Temperature control of drill is an important aspect in the functioning of drill and is dependent on parameters rotation speed, torque, orthotropic site, sharpness of the cutting edges, irrigation, and cooling systems. The drill may consist of components including a physical drill, cord power, an electronically motorized bone drill, and a rotating bone shearing incision work unit. Drill can be integrated into the embodiments in a variety of manners.

Scalpel refers to a tool for slicing or cutting or osteotomy of bone during orthopedic procedure. The scalpel may be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate and performs cutting by an ultrasonically oscillating or forward/backward moving metal tip. Scalpel may prevent injuries caused by a drill in a spinal surgery such as complications such as nerve thermal injury, grasping soft tissue, tearing dura mater, and a mechanical injury may occur during drilling. Scalpel can be integrated into the embodiments in a variety of manners.

Stitches (also referred to as sutures) refers to a sterile, surgical thread used to repair cuts or lacerations and are used to close incisions or hold body tissues together after a surgery or an injury. Stitches may involve the use of a needle along with an attached thread. Stitches may be of type absorbable (the stitches automatically break down harmlessly in the body over time without intervention) and non-absorbable (the stitches do not automatically break down over time and must be manually removed if not left indefinitely). Stitches may be of type based on material monofilament, multifilament, and barb. Stitches may be classified based on size. Stitches may be of type based on material synthetic and natural. Stitches may be of various type based on coating of the stitches, including coated and un-coated. Stitches can be integrated into the embodiments in a variety of manners.

Stapler refers to a tool for fragment fixation when interfragmental screw fixation is not easy. When there is vast damage and bone is broken into fragments then staples can be used between these fragments for internal fixation and bone reconstruction. For example, they may be used around joints as in ankle and foot surgeries, in cases of soft tissue damage, to attach tendons or ligaments to the bone for reconstruction surgery. Stapler may be made of surgical grade stainless steel or titanium and they are thicker, stronger, and larger. The stapler can be integrated into the embodiments in a variety of manners.

Equipment refers to a set of articles, tools, or objects which help to implement or achieve an operation or activity. A medical equipment refers to an article, instrument, apparatus, or machine used for diagnosis, prevention, or treatment of a medical condition or disease or detection, measurement, restoration, correction, or modification of structure/function of the body for some health purpose. The medical equipment may perform functions invasively or non-invasively. The medical equipment may consist of components sensor/transducer, signal conditioner, display, data storage unit, etc. The medical equipment works by taking a signal from a measurand/patient, a transducer for converting one form of energy to electrical energy, signal conditioner such as an amplifier, filters, etc., to convert the output from the transducer into an electrical value, display to provide a visual representation of measured parameter or quantity, a storage system to store data which can be used for future reference. A medical equipment may perform any function of diagnosis or provide therapy, for example, the equipment delivers air/breaths into the lungs and moves it out of the lungs and out of lungs, to a patient who is physically unable to breathe, or breaths insufficiently. A medical equipment can be integrated into the embodiments in a variety of manners.

Ventilator (also referred to as a respirator) refers to an instrument that provides a patient with oxygen when they are unable to breathe on their own. The ventilator is required when a person is not able to breathe on their own. The ventilator may perform a function of pushing air into the lungs and allows it to come back out, gently like lungs when they are working. Ventilator functions by delivery of positive pressure to force air into your lungs, while usual breathing uses negative pressure by the opening of the mouth, and air flows in. The machine uses positive pressure to force air into your lungs. A ventilator may be required during surgery or after surgery. A ventilator may be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator may be used with a face mask (non-invasive ventilation, where the ventilation is required for a shorter duration of time) or with a breathing tube also referred to as an endotracheal tube (invasive ventilation, where the ventilation is required for a longer duration of time). A ventilator use may have some risks such as infections, fluid build-up, muscle weakness, lung damage, etc. A ventilator may be operated in modes ACV, SIMV, PCV, PSV, PCIRV, APRV, etc. A ventilator may have components including a gas delivery system, a power source, a control system, a safety feature, a gas filter, and a monitor. A ventilator can be integrated into the embodiments in a variety of manners.

Continuous positive airway pressure abbreviated as CPAP refers to an instrument which used for the treatment of sleep apnea disorder in a patient. Sleep apnea refers to a disorder in which breathing repeatedly stops and starts while a patient is sleeping, often because throat/airways briefly collapse or something temporarily blocks them and may lead to serious health problems, such as high blood pressure and heart trouble. Continuous positive airway pressure instrument helps patients with sleep apnea to breathe more easily during sleep by sending a steady flow of oxygen into the nose and mouth during sleep, which keeps the airways open and helps to allow normal breathing. The CPAP machine may work by a compressor/motor which generates a continuous stream of pressurized air which travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP may have a nasal pillow mask, nasal mask, or full mask. CPAP instrument may consist of components a motor, a cushioned mask, a tube that connects the motor to the mask, a headgear frame, and adjustable straps. The essential components may be a motor, a cushioned mask, and a tube that connects the motor to the mask. Continuous positive airway pressure instruments can be integrated into the embodiments in a variety of manners.

Consumables refer to necessary supplies for health systems to provide care within a hospital or surgical environment. Consumables may include gloves, gowns, masks, syringes, needles, sutures, staples, tubing, catheters, and adhesives for wound dressing, in addition to other tools needed by doctors and nurses to provide care. Depending on the device mechanical testing may be carried out in tensile, compression or flexure, in dynamic or fatigue, or impact or with the application of torsion. Consumables may be disposable (are time-saving, no risk of healthcare-associated infections, cost-efficient) or sterilizable (cross-contamination, risk of surgical site infections, sterilization). Consumables can be integrated into the embodiments in a variety of manners.

Robotic systems refer to systems that provide intelligent services and information by interacting with their environment, including human beings, via the use of various sensors, actuators, and human interfaces. These are employed for automating processes in a wide range of applications, ranging from industrial (manufacturing), domestic, medical, service, military, entertainment, space, etc. The adoption of robotic systems provides several benefits, including efficiency and speed improvements, lower costs, and higher accuracy. Performing medical procedures with the assistance of robotic technology are referred to as medical robotic systems. The medical robotic system market can be segmented by product type into Surgical Robotic Systems, Rehabilitative Robotic Systems, Non-invasive Radiosurgery Robots, and Hospital and Pharmacy Robotic Systems. Robotic technologies have offered valuable enhancements to medical or surgical processes through improved precision, stability, and dexterity. Robots in medicine help by relieving medical personnel from routine tasks, and by making medical procedures safer and less costly for patients. They can also perform accurate surgery in tiny places and transport dangerous substances. Robotic surgeries are performed using tele-manipulators, which use the surgeon's actions on one side to control the "effector" on the other side. A medical robotic system ensures precision and may be used for remotely controlled, minimally-invasive procedures. The systems comprise computer-controlled electromechanical devices that work in response to controls manipulated by the surgeons. Robotic systems can be integrated into the embodiments in a variety of manners.

An Electronic Health Record (EHR) refers to a digital record of a patient's health information, which may be collected and stored systematically over time. It is an all-inclusive patient record and could include demographics, medical history, history of present illness (HPI), progress notes, problems, medications, vital signs, immunizations, laboratory data, and radiology reports. A computer software is used to capture, store, and share patient data in a structured way. The EHR may be created and managed by authorized providers and can make health information instantly accessible to authorized providers across practices and health organizations—such as laboratories, specialists, medical imaging facilities, pharmacies, emergency facilities, etc. The timely availability of EHR data can enable healthcare providers to make more accurate decisions and provide better care to the patients by effective diagnosis and reduced medical errors. Besides providing opportunities to enhance patient care, it may also be used to facilitate clinical research by combining all patients' demographics into a large pool. For example, the EHR data can support a wide range of epidemiological research on the natural history of disease, drug utilization, and safety, as well as health services research. The EHR can be integrated into the embodiments in a variety of manners.

Equipment tracking systems, such as RFID, refers to a system that tags an instrument with an electronic tag and tracks it using the tag. Typically, this could involve a centralized platform that provides details such as location, owner, contract, and maintenance history for all equipment in real-time. A variety of techniques can be used to track physical assets, including Radiofrequency Identification (RFID), Global Positioning System (GPS), Bluetooth Low Energy (BLE), barcodes, Near-Field Communication (NFC), Wi-Fi, etc. The equipment tracking system comprises the hardware components, such as RFID tags, GPS trackers, barcodes, and QR codes. The hardware component is placed on the asset, and it communicates with the software (directly or via a scanner), providing it with data about the asset's location and properties. An equipment tracking system uses electromagnetic fields to transmit data from an RFID tag to a reader. Reading of RFID tags may be done by portable or mounted RFID readers. RFID may be very short for low frequency or high frequency for ultra-high frequency. Managing and locating important assets is a key challenge for tracking medical equipment. Time spent searching for critical equipment can lead to expensive delays or downtime, missed deadlines and customer commitments, and wasted labor. The problem has been solved by the use of barcode labels or using manual serial numbers and spreadsheets; however, these require manual labor. The RFID tag may be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own). Equipment tracking systems may offer advantages, no line of sight required, read Multiple RFID objects at once, scan at a distance, and flexibility. Equipment tracking systems, RFID can be integrated into the embodiments in a variety of manners.

Medical surgery is transitioning from the conventional process of making a long incision in the patient's body for performing surgery to the next generation of surgery, i.e., minimally invasive surgery ("MIS"). Continuous research will develop and integrate robotic instruments in a system that can be used for MIS purposes. Such integration can help a surgeon to perform surgery in an error-free manner, and at the same time, to work in a realistic environment that gives the surgeon a feel of conventional surgery. MIS is performed by making small incisions, in the range of 1-3 cm, in the patient's body and using pencil-sized instruments for the surgery. Most of the available robotic instruments used for MIS include straight, elongated shafts, from now on referred to as robotic arms, which enter into the patient's body through small incisions. The robotic arms can carry imaging equipment, such as a camera, and pencil-sized surgical instruments, such as forceps and scissors. The pencil-sized surgical instruments are also known as the end effectors. Further, the robotic arms are controlled from a robotic console which includes a robotic hand controller. The robotic hand controller receives input from the surgeon and controls the motion of the robotic arm. In the present state of the art, the surgeon controls the robotic arm using a hand controller. However, the human wrist is capable of three degrees of freedom, whereas the robotic arms provide more than four degrees of freedom at the site of surgery. Surgeons may rely on visual feedback to monitor the movement of the robotic arm and end effector to ensure the correct actions are taken.

Quantum computing refers to any computational device or method which utilizes properties of quantum states defined by quantum mechanics such as superposition, entanglement, etc. to perform computations. These devices utilize qubits which are the quantum equivalent to bits in a classical computing system, comprised of at least two quantum states or probable outcomes. These outcomes, combined with a coefficient representing the probability of each outcome, describes the possible states, or bits of data, which can be represented by the qubits according to the principle of quantum superposition. These states may be manipulated which may shift the probability of each outcome or additionally add additional possible outcomes to perform a calculation, the final state of which can be measured to achieve the result.

Quantum computing provides significant benefits in the areas of encryption and the simulation of natural systems. Encryption is aided by the uncertain nature of quantum computing in that data is represented by an indeterminate state of probable outcomes, therefore making decryption virtually impossible. The simulation of natural systems, such as chemical and biological interactions, benefit from the fact that nature of quantum computing is the same as the systems being simulated. In medical fields, quantum computing shows the greatest promise for drug discovery and simulating the interaction of drugs with biologic systems, however the same technology might be used to predict the interaction of a biologic system with an implanted device, preventing rejection of an implant by a patient's body, long term function of an implant, and potentially the reaction of a patient to a surgical procedure during a simulation before a procedure or actively during a procedure.

SUMMARY

The present disclosure is generally directed to technology to assist with performing surgical procedures using robotic surgical tools by automatically adjusting user feedback, such as haptic feedback provided through robotic surgical tool control devices, based on how closely one or more aspects of a predetermined surgical plan matches detected conditions during the surgical procedure. For example, a surgical plan that is used to guide and control a robotic surgical tool during a surgical procedure can be generated in advance of performing the procedure, such as being generated hours, days, and/or weeks in advance of a surgery. The surgical plan can be generated based on conditions that, at the time of generating the plan, exist within the patient, such as the size, location, and/or number of tumors to be removed during a procedure. However, conditions within the patient may change between when the plan is generated and when the surgery is performed. For example, a tumor may change in size between when the plan was generated and when the surgery is performed. In such instances, the predetermined surgical plan and the guidance it provides to the robotic surgical tool operator, such as defining boundaries around anatomical structures to be excised and/or to avoid contacting, may be less accurate and reliable for performing the surgery, and in some instances may lead to potentially bad patient outcomes if undetected by a surgeon. The disclosed technology can provide solutions to these and/or other problems, as described throughout this document, by automatically detecting instances where patient conditions have deviated from those present during surgical planning generation and taking corrective/preventative actions, such as adjusting and/or providing haptic feedback to a surgeon operating a robotic surgical tool.

For example, touch and tactile feedback can be critical for surgeons because it may provide additional information, such as tactile sensing of tissue palpation, that a surgeon may use to perform a surgical procedure. Providing real-time haptic feedback to a surgeon during a procedure can overcome the loss of touch that comes from robotically assisted surgery. For example, robotic surgical control devices can be configured to provide force feedback, which is a modality of haptic feedback that conveys a kinesthetic sensation to the surgeon when the end effector of a robotic surgical tool interacts with a tissue or with a navigational boundary. The disclosed technology can include a haptic interface coupled with the robotic hand controller to provide force feedback to the surgeon, greater accuracy and real-time adjustment to changes in surgical conditions and patient status can be achieved. The robotic hand controller and haptic interface can be used to control a robotic surgical tool and to receive force feedback from the robotic arms that the surgeon, which can used to improve the surgery in real-time.

As mentioned above, the human wrist is capable of three degrees of freedom, whereas the robotic arms may provide more than four degrees of freedom at the site of surgery. However, in conventional existing systems, force feedback may not be received in any available degrees of freedom.

Due to the absence of force feedback, the surgeon may be forced to rely solely on the robotic console monitors' visual feedback and does not get a real feel of conventional surgery. Accordingly, while robotic surgical systems offer greater precision and can be used in carrying out minimally invasive surgical procedures, conventional systems may not allow the surgeon to use their tactile senses during robotic surgeries in the same way that they can during a conventional surgery. In contrast, the disclosed technology can improve upon conventional systems, for example, by providing force feedback and, additionally, dynamically adapting the force feedback based on the accuracy of the pre-surgical plans to the actual conditions encountered during a surgical procedure, which can provide tactile feedback to better guide and direct surgeons performing robotic surgical procedures. The disclosed technology can use any of a variety of sensors and/or force feedback devices in association with minimally invasive surgery devices and/or robotic surgical tools to provide tactile feedback, such as tactile sensations that can use different sense characteristics to convey any of a variety of information to a surgeon, such as shape, stiffness, and texture of organ or tissue. For example, force feedback sensors and devices can provide tactile feedback indicating the presence of a tumor through a "tougher" feel than other surrounding healthy soft tissue, the presence of blood vessels through a "pulse" feel conveyed to the user, and the presence of abnormal lesions that a surgeon can feel through the use of tactile sensation. Such sensors can provide tactile feedback in any of a variety of ways, such as providing output shape, size, pressure, softness, composition, temperature, vibration, shear, and/or normal forces.

The disclosed technology can use image-based feature comparison to determine the accuracy of a pre-surgical plan to conditions encountered during a surgical procedure. For instance, image-guided surgery can combine pre-surgical imaging and planning with intra-operative guidance and visualization, which can include comparing pre-operative imaging to intra-operative imaging to account for changes, such as organ shift since the pre-operative images were generated, or inaccuracies in those images. For example, a surgical procedure to be carried out with a robotic surgical tool can be planned using pre-surgical images of the surgical site that depict anatomical features of the patient relevant to the surgery. Before the surgery begins, thresholds can be established about the anatomical features as boundaries that should not be crossed by the robotic surgical tool, and navigational data can be stored that will aid in the surgery. After surgery has begun, sensors and cameras in the operating room can capture intra-operative images of the same anatomical features of the patient to determine whether there has been movement or change in the position of the features relative to the pre-surgical images. Differences in the images can change a confidence level in the original surgical plan, and can be used to change the surgical thresholds, for example by increasing the size of the boundary about the anatomical feature so that the robotic surgical tool will be inhibited from approaching the feature beyond the boundary. Haptic feedback can also be provided to the surgeon at a haptic interface when the robotic surgical tool approaches or surpasses the threshold, getting too close to the anatomical feature. This real-time adjustment of the surgical plan and haptic feedback levels enables better surgical outcomes because the surgeon can be better aware of the status of the surgical site, even when performing surgery using a robotic surgical system.

In one implementation, a method for adjusting haptic feedback during surgery with a robotic surgical tool includes accessing, by a computing device, a predetermined surgical plan for a surgical procedure to be performed on a patient using a robotic surgical tool. The predetermined surgical plan identifies and includes (i) a surgical proximity threshold that is used to determine one or more boundaries for the robotic surgical tool during the surgical procedure and (ii) one or more pre-surgical images of the patient that depict one or more anatomical features of the patient at or around a surgical site for the surgical procedure. The pre-surgical images of the patient were captured before commencing the surgical procedure. The method can further include receiving, from a sensor, an intra-operative image of the one or more anatomical features of the patient at or around the surgical site, wherein the intra-operative image is captured during the surgical procedure; and comparing, by the computing device, depictions of the one or more anatomical features in the one or more pre-surgical images and the intra-operative image. The method can additionally include determining, based on the comparison, a confidence level for the predetermined surgical plan during the surgical procedure. The confidence level can indicate a degree to which positions of the one or more anatomical features of the patient at or around the surgical site differ between the one or more pre-surgical images and the intra-operative image. The method can further include adjusting the surgical proximity threshold of the robotic surgical tool based on the confidence level; and providing haptic feedback to a haptic interface based on a position of the robotic surgical tool with respect to the adjusted surgical proximity threshold. A level of haptic feedback to be provided when the robotic surgical tool approaches or passes the adjusted surgical proximity threshold can be determined based on the confidence level. The method can further include controlling the robotic surgical tool based on the adjusted surgical proximity threshold and confidence level to limit a movement of the robotic surgical tool past the adjusted surgical proximity threshold.

Such a method can optionally include one or more of the following features. The comparing depictions of the one or more anatomical features in the one or more pre-surgical images and the intra-operative image can further include: determining, based on the surgical plan, a first reference point of the pre-surgical image; detecting, at the computing device, a first position of the first reference point in the pre-surgical image; detecting, at the computing device, a second position of a corresponding second reference point in the intra-operative image; and determining a distance between the first reference point and the second reference point. The first reference point and the corresponding second reference point can be an aspect of the one or more anatomical features of the patient at or around a surgical site for the surgical procedure. Determining the confidence level can further include calculating, based on the distance, a confidence interval width; and accessing from the predetermined surgical plan a size of movement required by the robotic surgical tool to complete the surgical procedure. The surgical plan can further include a workflow including a plurality of steps for completion of the surgical procedure, and wherein the determining the confidence level and adjusting the surgical proximity threshold occurs at least before commencing each of the plurality of steps. Adjusting the surgical proximity threshold can include adjusting the surgical proximity threshold for one of the plurality of steps of the workflow. Adjusting a surgical proximity threshold can include receiving, from one of a predetermined value or a user input, a first surgical proximity threshold establishing a first boundary at a first distance around a first anatomical feature; and in response to determining the confidence level for the predetermined surgical plan, updating the first surgical proximity threshold to a second surgical proximity threshold in proportion to the confidence level. The second surgical proximity threshold can establish a second boundary at a second distance around the first anatomical feature, the first distance being different than the second distance.

The method can further include detecting, at a sensor, a position of the robotic surgical tool relative to the first anatomical feature; determining that the position of the robotic surgical tool is within the second boundary established by the second surgical proximity threshold; and providing haptic feedback at a feedback level determined by the distance of the position of the robotic surgical tool from the first anatomical feature. The sensor can be integrated with the robotic surgical tool and is configured to determine a relative position of the robotic surgical tool relative to a predetermined reference point of the first anatomical feature of the patient. The haptic feedback can be provided at the haptic interface configured to allow input of instructions to control movement of the robotic surgical tool within the surgical site for the surgical procedure. The haptic feedback can be provided at the interface in response to certain movements of the robotic surgical tool within the surgical site is one of a vibration, pushback force, pressure, softness, temperature, shear and normal forces.

The method can further include setting a first level of haptic feedback associated with a first step of the plurality of steps of the workflow before commencing the surgical procedure; and prior to beginning the first step of the workflow during surgery, adjusting the first level of haptic feedback proportionally to the confidence level. Providing haptic feedback at the haptic interface can include: increasing a vibration frequency at the haptic interface in proportion to the confidence level; and providing the increased vibration frequency at the haptic interface in response to determining that the robotic surgical tool crossed a boundary indicated by the adjusted proximity threshold. The method can further include providing a lower level of haptic feedback than the increased vibration frequency at the haptic interface in response to determining that the robotic surgical tool is not within the boundary indicated by the adjusted proximity threshold. The lower level of haptic feedback can be based on the first level of haptic feedback and a distance of the robotic surgical tool from the boundary. Controlling the robotic surgical tool can be based on the adjusted surgical proximity threshold further comprises restricting a speed or range of movement of the robotic surgical tool in proportion to the confidence level. Providing haptic feedback at a haptic interface can include providing a vibrational frequency at one of a joystick, computer mouse, or wearable haptic interface. The method can further include receiving, from at least one additional sensor, at least one health parameter of a patient; and generating for display on a display monitor the at least one health parameter of the patient.

In another implementation, a system for adjusting haptic feedback during surgery with a robotic surgical tool includes a database comprising data storage for storing a predetermined surgical plan for a surgical procedure to be performed on a patient using a robotic surgical tool. The predetermined surgical plan can identify and include (i) a surgical proximity threshold that is used to determine one or more boundaries for the robotic surgical tool during the surgical procedure and (ii) one or more pre-surgical images of the patient that depict one or more anatomical features of the patient at or around a surgical site for the surgical procedure. The pre-surgical images of the patient can be captured before commencing the surgical procedure. The system can further include a robotic surgical tool including an end effector for performing the surgical procedure and at least one location sensor for detecting a position of the robotic surgical tool. The system can additionally include a surgical sensor positioned to capture intra-operative images of the one or more anatomical features of the patient at or around a surgical site during the surgical procedure. The system can further include a controller of the robotic surgical tool, the controller comprising a haptic interface configured to receive haptic feedback throughout the surgical procedure when the end effector of the robotic surgical tool approaches the one or more boundaries for the robotic surgical tool, the controller further configured to receive instructions for movement of the robotic surgical tool as inputs and transmit the instructions for movement to the robotic surgical tool. The system can additionally include a robotic surgical tool, the robotic surgical tool including an end-effector and a controller; at least one sensor configured to obtain intra-operative images and data; and a computing device, the computing device communicatively coupled to the database, surgical sensor, and to the controller of the surgical robot. The computing device can be configured to: access the predetermined surgical plan including the one or more pre-surgical images from the database; receive, from the surgical sensor, an intra-operative image of the of the one or more anatomical features patient at or around the surgical site, wherein the intra-operative image is captured during the surgical procedure, compare depictions of the one or more anatomical features in the one or more pre-surgical images and the intra-operative image; determine based on the comparison, a confidence level for the predetermined surgical plan during the surgical procedure, wherein the confidence level indicates a degree to which positions of the one or more anatomical features of the patient at or around the surgical site differ between the one or more pre-surgical images and the intra-operative image; adjust the surgical proximity threshold of the robotic surgical tool based on the confidence level; provide haptic feedback to the haptic interface based on a position of the robotic surgical tool with respect to the adjusted surgical proximity threshold, wherein a level of haptic feedback to be provided when the robotic surgical tool approaches or passes the adjusted surgical proximity threshold is determined based on the confidence level; and control the robotic surgical tool based on the adjusted surgical proximity threshold and confidence level to limit a movement of the robotic surgical tool past the adjusted surgical proximity threshold.

Such a system can optionally include one or more of the following features. The computing device can be further configured to: determine, based on the surgical plan, a first reference point of the pre-surgical image; detect a first position of the first reference point in the pre-surgical image; detect a second position of a corresponding second reference point in the intra-operative image; and determine a distance between the first reference point and the second reference point. The first reference point and the corresponding second reference point can be an aspect of the one or more anatomical features of the patient at or around a surgical site for the surgical procedure. The computing device can be further configured to: calculate, based on the distance, a confidence interval width; and access from the predetermined surgical plan a size of movement required by the robotic surgical tool to complete the surgical procedure. The surgical plan can further include a workflow including a plurality of steps for completion of the surgical procedure, and wherein the determining the confidence level and adjusting the surgical proximity threshold occurs at least before commencing each of the plurality of steps. The computing device can be further configured to: receive, from one of a predetermined value or a user input, a first surgical proximity threshold establishing a first boundary at a first distance around a first anatomical feature; and update, in response to determining the confidence level for the predetermined surgical plan, the first surgical proximity threshold to a second surgical proximity threshold in proportion to the confidence level. The second surgical proximity threshold can establish a second boundary at a second distance around the first anatomical feature, the first distance being different than the second distance.

The disclosed technology can provide any of a variety of advantages. For example, surgical outcomes can be improved by the use of image-guided surgery in combination with sensors that can indicate to the surgeon through provided haptic feedback a position of the robotic surgical tool end effector relative to various anatomical features of the patient in the surgical site. Furthermore, surgical outcomes can further be improved by dynamically adjusting and providing haptic feedback to surgeons in response to detecting deviations between intra-surgical conditions and those that were expected and/or upon which a pre-surgical plan was based, such as the positioning, size, and/or condition of anatomical features included in a pre-surgical plan being different during the surgery than during their pre-surgical assessment. Dynamic adjustments and modifications to haptic feedback in real time during the surgical procedure can help guide surgical procedures in ways that better account for such changes in a patient's condition between a pre-surgical planning stage and the intra-surgical stage, which can lead to better surgical and patient outcomes.

In another example, real-time comparison of pre-surgical images and plans to images obtained during a surgery enable a surgeon and/or robotic surgical instrument control to react to alterations or changes in the surgical field. By processing the comparison of images in real-time to obtain confidence levels of surgical plans and navigation, the surgery can be modified to accommodate changes and differences between the pre-surgery and during surgery images by one or more of altering the surgical navigation control, increasing tolerances surrounding markers, providing increased haptic feedback to a surgeon, and increasing a frequency of comparison of images. Altering the surgery to reflect the differences in the pre-surgery and real-time images provides critical information to a surgeon and increases the accuracy of a surgery, leading to improved outcomes.

The details of one or more implementations are set forth in the accompanying drawings and the description below. Other features and advantages will be apparent from the description and drawings, and from the claims.

DESCRIPTIONS OF THE DRAWINGS

DETAILED DESCRIPTION

Embodiments of the present disclosure will be described more thoroughly from now on with reference to the accompanying drawings. Like numerals represent like elements throughout the several figures, and in which example embodiments are shown. However, embodiments of the claims may be embodied in many different forms and should not be construed as limited to the embodiments set forth herein. The examples set forth herein are non-limiting examples and are merely examples, among other possible examples.

Figure 1:
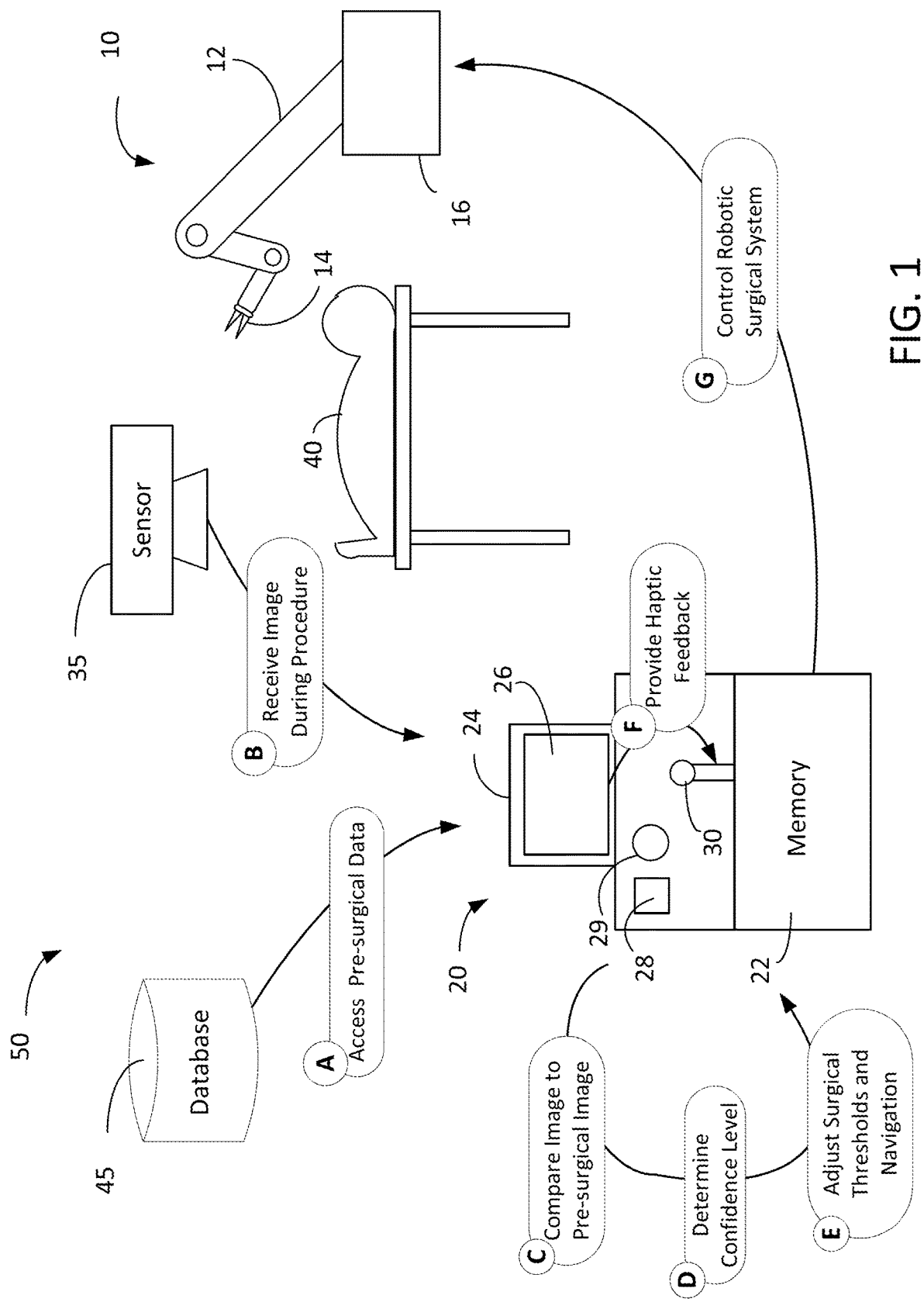
FIG. 1 shows an example system and process for providing real-time adjustment of haptic feedback during a surgery conducted by a surgical robot.

FIG. 1 depicts an example conceptual system 50 for providing real-time adjustment of haptic feedback during a surgery conducted by a surgical robot. The example system 50 includes an example robotic surgical tool 10, an operator device 20, a sensor 35, and a pre-surgical planning database 45.

The operator device 20 is configured to be used by an operator of the robotic surgical tool 10, such as a surgeon performing a surgical procedure. The operator device 20 can include any of a variety of computing devices (e.g., one or more processors) configured to receive user input to control the robotic surgical tool 10, to communicate and interface with the robotic surgical tool 10, and to present output information to the operator (e.g., surgeon), including providing visual, audible, and/or haptic feedback to the operator. The operator device 20 can include user interface components, such as a display housing 24 and a display screen 26 to present visual information, input devices 28 and 29 to receive user input (e.g., input to control the robotic surgical tool 10), a haptic interface 30 (which may be part of or separate from the input devices 28 and 29), and/or other interface components not depicted (e.g., speaker, microphone, wearable devices). The operator device 20 may be a collection of one or more separate devices that are in communication with each other, such as through wired connections and/or wireless connections between the components. For example, the input devices 28 and 29, and the haptic interface 30 may be wirelessly paired with a computing device that is part of the operator device 20, which can include memory 22 storing information relevant to the surgical procedure (e.g., surgical plan, pre-surgical imaging data, intra-surgical imaging data, instructions for automatically and dynamically adjusting parameters in real time during surgery).

The robotic surgical tool 10 includes a controller 16 that is configured to translate instructions from the operator device 20 into physical movements of one or more robotically controlled surgical components, such as an example robotic arm 12 and an end effector 14. Additional and/or alternative robotically controlled surgical components are also possible.

The system 50 is configured to perform a surgical procedure using a robotic surgical tool and a predetermined surgical plan, dynamically and automatically adjust aspects of the surgical plan during the surgery, and provide haptic feedback to a user during the surgery based on the adjusted aspects. An example process flow for providing these features is described with regard to steps A-G. At step A, the operator device 20 can access pre-surgical data stored in the pre-surgical planning database 45. The pre-surgical data includes pre-surgical images of the operating site on a patient, a pre-surgical plan including steps for carrying out the surgical procedure and navigational data, and patient data. The pre-surgical images are images that were obtained of the patient, surgical site on the patient's body, and anatomical features in or about the surgical site before the surgery is begun, for example at a pre-operative consultation. The images may be obtained and/or manipulated through the use of any of medical visualization systems, microscopes, fiber optics, surgical lights, cameras, sensors, imaging systems, X-ray systems, MRI, CT imaging, ultrasound imaging, fluoroscopy, or other imaging techniques. The images may be filtered, sized, and adjusted, and digital objects can be overlaid on the image to mark anatomical features and structures depicted in the image. Prior to surgery, the pre-surgical images can be used by a surgical planning module to plan the surgical work-flow, or the pre-surgical plan, including navigational data, routes, waypoints, and markers for use in moving through the surgical procedure. The surgical planning module is described in greater detail below, in FIGS. 2 and 3. After the operator device 20 accesses the pre-surgical images and data, the operator device 20 loads the pre-surgical data in the memory 22 for use to guide and direct the motions of the surgical robot 10 according to a plan outlined in the pre-surgical data. The operator device 20 may additionally display portions of the pre-surgical data on the display screen 26 to the user, such as showing a pre-surgical image of a target anatomical structure for the procedure (e.g., depicting tumor to be excised) and/or depicting a navigational path for the robotic surgical device 10.

At step B, the sensor 35 captures one or more images of the surgical field 40, which can include the surgical site of the patient during the surgery and transmits the intra-operative images to the operator device 20. The sensor 35 can be any of a variety of medical imaging sensors capable of obtaining images of a surgical site during a surgical procedure, and can be part of a broader imaging device and/or imaging system. For example, the sensor 35 can capture image (e.g., still images, sequences of images, videos) the surgical field 40 and/or the surgical site using any of a variety of imaging technologies, such as Real-time Fluorescence Imaging Topography Scanning (RFITS), tomograms, CT scans, ultrasound, radionuclide scans, arteriograms, x-rays, MRI, and/or other medical imaging technology. The intra-operative images provided by the sensor 35 can be stored by the operator device 20 and loaded in the memory 22, and may also be displayed to the user on the display screen 26.

The operator device 20 can use the intra-operative images from the sensor 35 in any of a variety of ways. For example, a navigation base module of the operator device 20, as described in greater detail below with regard to FIGS. 2 and 4, may access and use the intra-operative image data to identify a current position and progress of the surgical robot 10 along a navigational pathway that is part of the pre-surgical plan. In another example, as identified at step C, the operator device 20 can compare the intra-operative images to the pre-surgical images. The operator device 20 can perform the comparison using any of a variety of features in the images. For example, the operator device 20 can compare particular reference points of the subject matter of the images, for example anatomical features within the images, or navigational points superimposed over the image. The comparison performed by the operator device 20 can yield one or more metrics indicating a level of similarity or difference between the images, such as determining a distance between reference points of the intra-operative images and the pre-surgical images. The operator device 20 may perform any of a variety of image processing steps before performing the comparison to place the pre-surgical images and the intra-operative images into a common image-space for ready comparison (e.g., scaling, rotating, filtering). The operator device 20 to can use any of a variety of image comparison techniques, such as using one or more machine learning algorithms and trained machine learning models to detect differences in the images (e.g., neural networks algorithms, such as convolution neural networks), using image-based object detection techniques, comparing component parts of the images (e.g., comparison on a pixel-by-pixel basis, calculates a cross-correlation in the spatial and frequency domain of the images), and/or other image comparison techniques. Differences between the positioning of anatomical features in the images can indicate that the patient's anatomical condition has changed since the pre-surgical images were captured and used to generate the pre-surgical data, such as being due to organ shift and/or due to inaccuracies in the pre-operative images.

For example, the relative positions between organs, bones, blood vessels, nerves, and other anatomical structures will often be different in preoper imaging of a patient and intraoperative imaging. For instance, when a patient has a lumbar CT scan, preoperative images will often be captured while the patient is in a supine position. However, intraoperatively such patients will often be placed in other positions, like lateral or prone, where the soft tissues, organs, and skeletal structures change positions from the supine position. Furthermore, intraoperatively during a procedure, the relative positioning can change as well depending on, for example, trunk/limb positioning changes and whether a cavity is pressurized/insuflated, such as with CO2 for laparoscopic surgery and saline for arthroscopic or endoscopic surgery. Such changes can potentially frustrate the use of a pre-surgical plan, which the disclosed technology can remedy to ensure safe and effective execution of the pre-surgical plan regardless of changes.

At step D, based on the determined differences between the pre-surgical and intra-operative images, the operator device 20 determines a confidence level for the pre-surgical plan. As will be described in detail below, the confidence level can be a measure of how closely the pre-surgical image corresponds to the intra-operative image. A high confidence value can indicate that the pre-surgical imaging is closely correlated to the current intra-surgical imaging—meaning that the assumptions for the surgical procedure included pre-surgical plan continue to be accurate and that the pre-surgical plan can be followed closely. In contrast, a low confidence value can indicate that the intra-operative images are not closely correlated with the pre-surgical images—meaning that the assumptions for the surgical procedure (based on the pre-surgical images) included in the pre-surgical plan may no longer be accurate, and that the pre-surgical plan may not fit the current operating conditions. The confidence level may be determined overall for the surgical plan and/or component parts thereof, such as a confidence level associated with a current step in the surgical plan workflow based on comparison of relevant reference points to the current step. As discussed above, there can often be a large degree of shift in the relative positioning of anatomical structures from pre-surgical/preoperative imaging to intraoperative imaging. As a result, the pre-surgical plan may be modified from pre-surgical imaging to intraoperative imaging in order to be safe, and the plan can be also be modified due to position changes noticed during the actual surgery.

The confidence level can be determined using any of a variety of techniques. For example, a registration module of the operator device 20 may receive the intra-operative image data (e.g., step C described above) and determine the confidence in the surgical workflow based on the relative positions (and/or differences) of reference points in the pre-surgical and intra-operative images (e.g., step D). The registration module is described in greater detail below with regard to FIGS. 2 and 5. Any of a variety of techniques and/or components can be used to determine the confidence level, which may change over time as the surgical procedure proceeds according to the surgical plan. For example, a confidence level can be a statistical value based on combinations of comparisons between references points in the pre-surgical images and the intra-operative images (e.g., based on combination of difference values for five different reference points), such as a mean, median, standard deviation, maximum, minimum, and/or other statistical value derived from a combination of comparison values. In another example, confidence levels may be combined from comparison values over time, such as combining comparison values for images captured during a recurring time interval (e.g., images captured every 0.1 seconds, 0.2 seconds, 0.3 seconds, 0.5 seconds). Additional and/or alternate combinations of comparison values, as determined in Step C, are also possible. The confidence level can be provided along any of a variety of scales, such as a float value between 0.0 and 1.0, a plurality of enumerated values (e.g., low confidence value, medium confidence value, high confidence value), and/or other values.

At step E, the operator device 20 can adjust the surgical thresholds and/or navigation data based on the determined confidence level. For example, if the differences between the pre-surgical and intra-operative are extensive, a low confidence level can be determined and the surgical thresholds can be updated to reflect a lower tolerance for movements of the robotic tool (e.g., lower tolerance for the robotic tool 10 to deviate from a navigational pathway and/or to be positioned near particular anatomical features identified in the surgical plan). Conversely, if the differences between the pre-surgical and intra-operative images are minimal, the confidence level can be high and, as a result, the surgical thresholds can be updated to reflect a high tolerance for movements of the robotic tool (e.g., higher tolerance for robotic tool 10 to deviate from navigational pathway and/or to be positioned near particular anatomical features identified in the plan). The navigation data may also be updated based on the confidence level by altering the navigational data to more closely adapt to the positioning of anatomical features in the navigational data to reflect their positioning and/or characteristics in the intra-operative image. The operator device 20 may use any of a variety of modules and/or components to implement specific aspects of these adjustments. For example, a haptic module of the operator device 20, as described in greater detail below with regard to FIGS. 2 and 7, may adjust the surgical proximity thresholds, navigational data, and haptic responses in the surgical plan based on changes in the confidence level. Additionally and/or alternatively, the operator device 20 may transmit information about update thresholds and/or navigation information to the controller 16 of the robotic tool 10, which may impose restrictions and/or permissions on movements of the robotic tool 10 based on the adjusted values.

At step F, the operator device 20 provides a level of haptic feedback at the haptic interface 30 based on the adjusted thresholds and adjusted navigation data determined at step E. The haptic interface 30 may part of a control interface, such as a joystick, computer mouse, or wearable haptic interface such as a glove, headset, suit, virtual reality motion controllers, smart ring, smart watch, smart glasses, and/or generic haptic devices (e.g., coin-sized device that can wirelessly receive notifications and provide haptic feedback to the surgeon) that can be attached to surgeon's location of preference, such as a face mask, lapel, belt, socks, shoes, and/or other locations. The haptic feedback can include any of a variety types of tactile feedback, such as varying levels, patterns, and/or durations of vibration, pushback and/or resistive force, and/or other tactile indications provided to the operator, such as tactile indicating a position of the end effector 14 relative to anatomical features within the surgical field using the adjusted thresholds and/or navigation based on determined confidence levels. The haptic feedback may further be an output indicative of any of a variety of features, such as shape, size, pressure, softness, stiffness, composition, temperature, vibration, shear, and normal forces associated with a position of the robotic surgical tool with regard to the anatomical features in and about the surgical site. Whether to provide haptic feedback and how much feedback to provide is determined based on the positioning of the robotic tool 10 and its component parts, such as the end effector 14, which can be determined based on the intra-operative images captured by the sensor 35 and/or other positional sensor devices, such as integrated sensors the robotic tool 10 (e.g., infrared sensors integrated into the end effector 14) and/or devices positioned around the surgical field, such as laser positioning, magnetic, or other position-determining mechanisms. The haptic module of the operator device 20 may monitor the absolute or relative position of the robotic surgical tool 10, such as the position of the end effector 14 and/or the robotic arm 12, during a step of the surgical workflow or surgical plan, and deliver haptic feedback to the haptic interface 30 based on the position. For instance, haptic feedback can be provided to warn and/or prevent an operator from moving the robotic tool 10 within an adjusted threshold distance from an anatomical feature identified to not be contacted by the robotic tool 10 in the surgical plan. The haptic module is described in greater detail below in FIGS. 2 and 7.

For example, the sensor 35 may obtain an image which depicts the position of the end effector 14 relative to a relevant anatomical feature and transmit the image to the operator device 20. The operator device 20 can then determine a distance between the end effector 14 position and the relevant anatomical feature based on data received from sensors, determine whether the distance is within one or more surgical proximity thresholds and determine an amount of haptic feedback to provide through the haptic interface 30 based on the one or more surgical proximity thresholds satisfied by the distance. An initial haptic feedback threshold or level may be set by the user, or may be predetermined by the manufacturer. The user or manufacturer set level can be a maximum level or minimum level of haptic feedback to be provided. In some implementations, the amount and type of haptic feedback provided at the haptic interface can be based, for example, on a percentage of the set maximum level based on the determined distance between the location of the end effector 14 and the relevant anatomical structure and taking into account the adjusted thresholds and navigational data.

At step G, the operator device 20 can transmit instructions to control the robotic surgical system 10 based on the adjusted thresholds and navigation levels. The instructions controlling the robotic surgical system 10 can be received by the operator device 20 as user inputs to the first input 28 and second input 29 and to the haptic interface 30, or as an input by the user at the haptic interface 30. The first input 28 and the second input 29 can be different example types of user input devices, such as keyboards, microphones, cameras, motion-based input devices, a computer mouse, a joystick, and/or other appropriate input devices. The first and second input devices 28 and 29 can, in some instances, be part of the haptic interface 30, and/or they may be separate. In some instances, there may not be present and only the haptic interface 30 may be provided.

The operator device 20 and/or the surgical tool 10 can alone, or in combination, enforce compliance with the updated thresholds and navigation levels during the surgery, including modifying them as the surgical procedure progresses. For example, the operator device 20 can automatically restrict the instructions that are transmitted at Step G to control the robotic surgical tool 10 to only those instructions that will comply with the adjustments to the threshold and navigation, so as to follow a modified surgical plan. In this example, the haptic feedback that is provided via the haptic interface 30 can be determined by the operator device 20. For instance, if the input provided by the surgeon would cause one or more motions of the robotic tool 10 to not comply with the adjusted thresholds and/or navigation, the operator device 20 can provide appropriate haptic feedback to the surgeon indicating those movements are not currently permitted and can also block instructions to perform those movements from being transmitted to the robotic tool 10.

In another example, the operator device 20 can transmit instructions to the robotic tool 10, which the robotic surgical system 10 and its controller 16 can use to restrict and/or permit the instructed motions of the robotic surgical system 10 so that they comply with the modified thresholds and/or navigation. In this example, the operator device 20 may send all control commands that are received via the user input devices to the robotic tool 10, and the robotic tool 10 and its controller 16 can determine whether those movements and/or operations are permitted based on the modified thresholds and/or navigation. The robotic tool 10 can provide responses back to the operator device 20 indicating whether and to what extent the robotic tool 10 is following the user commands (e.g., moving robotic arm as commanded, not moving robotic arm as commanded, moving robotic arm less than or in different way than commanded), which the operator device 20 can translate into haptic feedback provided to the surgeon via the haptic interface 30. For instance, if the operator device 20 directs the robotic arm to move laterally 2 cm but this movement would fail to comply with the modified thresholds and/or navigation for the procedure, as communicated to the robotic tool 10, the controller 16 for the robotic tool 10 can ignore the command (not perform the commanded movement) and can transmit a signal back to the operator device 20 indicating that the command would not be followed. The operator device 20 can translate that signal from the robotic tool 10 into haptic feedback provided to the surgeon via the haptic interface 30, such as providing vibrations and/or restricting/pushing back against the user movement of the controller. The robotic tool 10 may provide other feedback beyond simply whether or not the command was performed/permitted under the modified thresholds and/or navigation, such as indications when the tool 10 is within a threshold distance of various reference points.

In another example, the operator device 20 and the robotic tool 10 can both enforce compliance with the modified thresholds and/or navigation, combining the two examples in the preceding paragraphs. The operator device 20 can perform its own compliance enforcement and, in instances where commands are determined to be in compliance by the operator device 20 and transmitted to the robotic tool 10, then the robotic tool 10 can additional determine whether the command complies with the modified thresholds and/or navigation—providing two layers of compliance monitoring and enforcement to ensure safe operation of robotic tool based on the determined confidence levels. Other configurations are also possible.

Figure 2:
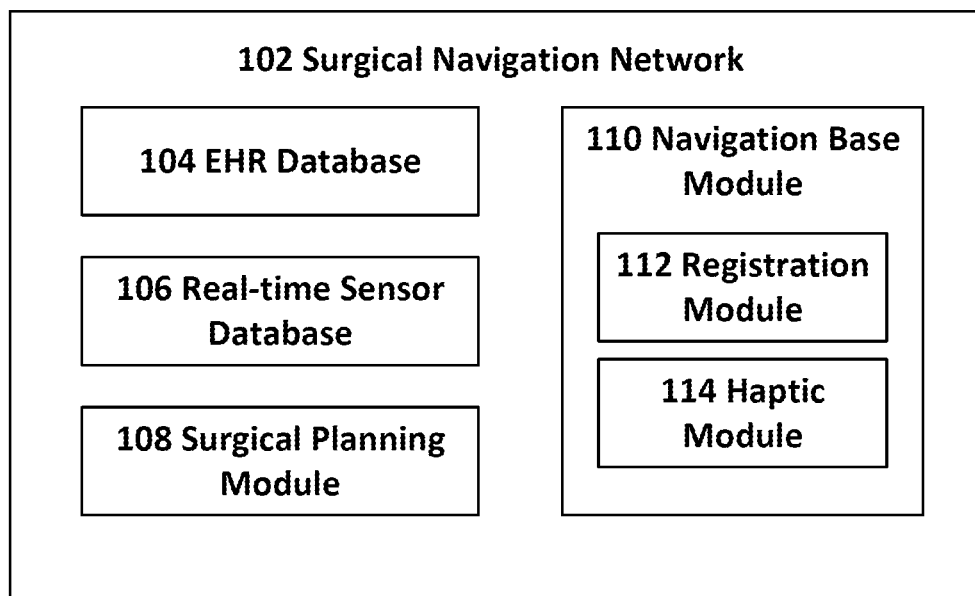
FIG. 2 shows a box diagram of components of a processor for providing real-time adjustment of haptic feedback in surgical robotics.
Figure 2:
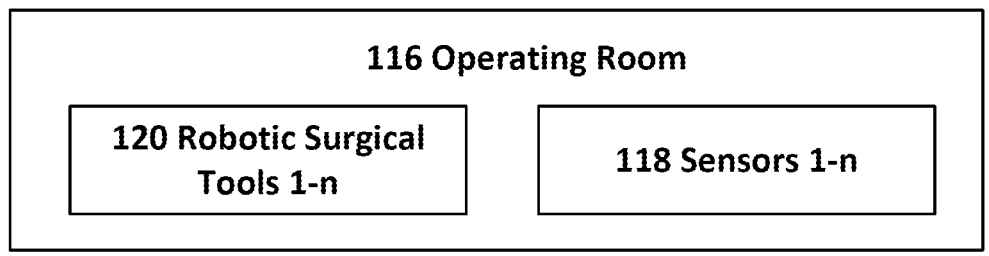

FIG. 2 depicts is an example system 100 for a real-time adjustment of haptic feedback in surgical robotics. The system 100 can be similar to the system 50 described above with regard to FIG. 1, and can be used to perform the steps described above with regard to FIG. 1.

The example system 100 can include of a surgical navigation network 102 (e.g., operator device 20) that is communicatively coupled to at least one robotic surgical tool 120 (e.g., robotic surgical tool 10) and at least one sensor 118 (e.g., sensor 35) monitoring a surgical procedure in an operating room 116 to adjust the haptic feedback to the surgeon from the robotic surgical tool 120 in response to changes in the confidence level in the pre-operative surgical plan in response to real-time data from one or more sensors 118. The surgical navigation network 102 may allow for the creation of surgical plans, including navigational data, through the surgical planning module 108 based on pre-operative image data.

In some embodiments, the surgical navigation network 102 includes a database 104, such as an EHR database maintained by one or more remote server systems, a local data repository of patient records, encrypted and distributed medical data (e.g., blockchain medical data), and/or other data storage systems, that may contain patient records. Electronic health records can include digital medical records for patients, such as a digital version of a patient's paper chart, pre-surgical imaging of the patient, and/or other medical data. The database 104 (e.g., EHR database) may contain more information than a traditional patient chart, including but not limited to, patient's medical history, diagnoses, medications, treatment plans, allergies, diagnostic imaging, lab results, etc. In one embodiment, the steps for each procedure may be stored in the database 104. Some steps in the procedure may include navigational data to communicate the position of a portion of the patient's anatomy and the robotic surgical tool 120 next direction or function.

In some embodiments, the surgical navigation network 102 includes a real-time sensor database 106 that may store the output of one or more sensors 118 during a given surgical procedure. For example, Real-time Fluorescence Imaging Topography Scanning (RFITS) may be used to determine the boundaries of a tumor during surgery. Other intra-operative data collection, such as plain films, tomograms, computed tomographic scans, ultrasound, radionuclide scans, arteriograms, magnetic resonance imaging, cameras attached to the surgical manipulators or end effectors, cameras mounted to the ceiling or other above the surgical theater, cameras that may be mounted on a tripod or other independent mounting device, cameras that may be body worn by the surgeon or other surgical staff, cameras that may be incorporated into a wearable device, such as an augmented reality device like Google Glass, cameras that may be integrated to an endoscopic, microscopic, laparoscopic, or any camera or other imaging device (e.g. ultrasound) that may be present in the surgical theater.

In some embodiments, the surgical navigation network 102 includes a surgical planning module 108 that allows a surgeon to create a workflow for a surgical procedure based, at least in part, on pre-operative imaging data in the database 104. Surgical workflows can include route planning based on pre-operative imaging. Navigational data, such as routes, waypoints, markers, etc., may be included in a surgical plan. For example, a CT scan may be used to identify the boundary between a tumor to be removed and the healthy tissue surrounding it. The surgical planning module 108 may allow for proximity thresholds to be defined for given anatomical features in the patient for one or more steps in the procedure. In one embodiment, the amplitude and type of haptic feedback to the surgeon through the robotic surgical tools 120 may be defined for one or more of the proximity thresholds. For example, in a partial knee replacement, a surgeon may indicate they do not wish to come within 5 mm of the Popliteus muscle with the burr being used to remove a portion of the lateral condyle of the patient's right tibia. The surgeon may define that threshold and the type (vibration) and amplitude (30 Hz) of haptic feedback they should receive if the burr comes within 5 mm of the Popliteus muscle. Guidance can additionally and/or alternatively be presented visually in an interface to a surgeon using any of a variety of features. For example, an interface can be presented to a surgeon during spine navigation that includes CT images (2D and/or 3D images) and the tool position can be indicated by a virtual overlay onto these images. The other structures, like blood vessels and nerves, may be annotated in their visual interface, such as through coloring the structures in the interface (e.g., blood vessels are colored red, veins purple/blue), which may be considered "no go" zones for the procedure unless specifically called out for operation.

In some embodiments, the surgical navigation network 102 includes a navigation base module 110 that may provide procedure and patient-specific guidance to the surgeon operating a robotic surgical tool 120. The surgical workflow created through the surgical planning module 108 may include navigational data based upon pre-operative imaging. The navigation base module 110 receives intra-operative image data. In one embodiment, the intra-operative image is collected continuously. In one embodiment, intra-operative image data is captured at the request of the surgeon. The intra-operative image data may be sent to the registration module 112 to determine the pre-operative navigation data's confidence in the surgical workflow based on the relative position of reference points in the intra-operative image. The confidence level and navigation data may then be used by the haptic module 114 to adjust the proximity thresholds in the workflow for a given navigational data point based on the confidence level. The closer the intra-operative image is to the pre-operative image, the higher the confidence level. The higher the confidence level, the more closely the proximity threshold(s) and haptic response(s) in the pre-operative workflow can be followed. The lower the confidence level, the greater the level of caution needed. This confidence level may result in higher proximity threshold(s) and stronger haptic feedback response(s). The navigation base module 110 prompts the registration module 112 with each new intra-operative image in the real-time sensor database 106. Embodiments may include a registration module 112, which may compare intra-operative image data in the real-time sensor database 106 with pre-operative image data from the database 104. Image registration has been used in image-guided surgery. This module may calculate a confidence level for a given navigation point, such as the border of a tumor removed, based on the disparity in corresponding reference points in the two images. The calculation of the confidence level is described in greater detail below. Image registration can be performed in any of a variety of ways. For example, a marker can be placed on an immobile part of the skeleton, such as the pelvis. This marker can include an array of visible points fixed in space. The marker can also be fixed in space relative to the anatomy of interest, such as the lumbar spine, for example. Then, when an intraoperative CT scan is done which includes the reference marker array, the imaging data can be used to determine the intraoperative position of the spine relative to the markers. From this positioning information, additional tools and/or end effectors, each with their own array, can be tracked in space relative to the spine.

The navigation base module 110 also includes a haptic module 114, which may monitor the position of one or more robotic surgical tools 120 during a given step in a surgical procedure workflow. Haptic feedback is delivered to the controls of the robotic surgical tool(s) 120 based upon the absolute or relative position of one or more portions of the robotic surgical tool(s) 120. Haptic feedback can be used to mimic the feel of tissue through robotic controls, or as guidance-based haptics that keeps a tool on a defined path and prevents it from crossing a boundary. For example, a surgeon removing a brain tumor may not want his recission tool to progress past the tumor's barrier into the healthy brain tissue. A high-resolution image may be taken pre-operatively to identify the boundaries of the tumor. The tumor boundary may change due to the patient shifting on the operating table, or the pre-operative image may be flawed. An intra-operative image, which may be images or video captured from at least one of a plurality of imaging devices, such as, for example, cameras attached to the manipulators or end effectors, cameras mounted to the ceiling or other above the surgical theater, cameras that may be mounted on a tripod or other independent mounting device, cameras that may be body worn by the surgeon or other surgical staff, cameras that may be incorporated into a wearable device, such as an augmented reality device like Google Glass, cameras that may be integrated to an endoscopic, microscopic, laparoscopic, or any camera or other imaging device (e.g. ultrasound) that may be present in the surgical theater, may reinforce the pre-operative image's accuracy, or it may indicate a potential change in the position of the boundary between tumor and healthy tissue. The haptic module 114 adjusts the proximity thresholds and haptic responses in the workflow based on the imaging's confidence level determined by the registration module 112.

Proper surgical procedures require a sterile field. In some implementations, the sterile field is maintained in an operating room 116, or in a medical care facility such as a hospital, doctor's office, or outpatient surgery center. In the operating room 116, there may be one or more sensors 118 present, for example some number one (1) through n of sensors 118. Sensors 118, such as microphones, optical sensors, fluorescent imaging, CT scan, x-ray, ultrasound, etc., may be associated with one or more areas in the operating room 116. Sensors 118 may be associated with measuring a specific parameter of the patient, such as respiratory rate, blood pressure, blood oxygen level, heart rate, etc., as well as data related to the position of the patient's anatomy, such as tumors, the vascular system, bones, organs, nerves, muscles, soft tissue, etc. Sensors 118 may be communicatively coupled to the surgical navigation network 102 through a wired/direct connection, such as Ethernet, or wirelessly coupled through a cloud, Wi-Fi, or other wireless communications method. Sensors 118 may be used to identify discrepancies between pre-operative measurements or navigation markers and the present position or condition of the patient's anatomical features. Surgical procedures sometimes require one or more robotic surgical tools 120, such as fluorescence imaging, optoacoustic imaging, radiography, Raman spectrometry, thermoacoustic imaging, etc. In some embodiments, one or more of the surgical tools 120 may have one or more integrated sensors 118.

Figure 3:
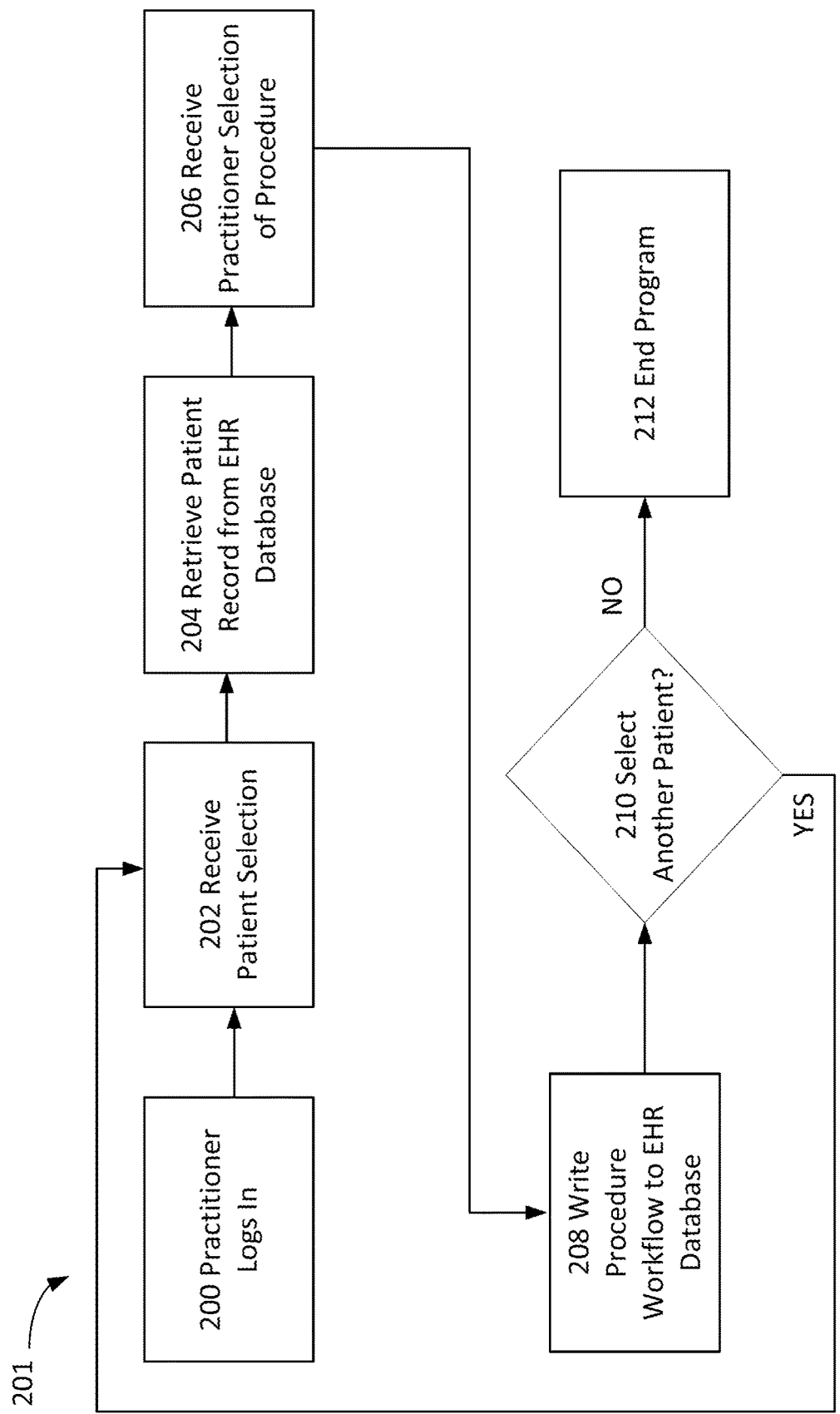
FIG. 3 shows a method for surgical planning.

FIG. 3 illustrates an example process utilized by the surgical planning module 108. The process begins when the practitioner, usually the doctor or surgeon performing the surgical procedure, logs in to the surgical navigation network 102, at step 200. The selection of a patient is received from the practitioner at step 202. The selected patient's electronic health record is retrieved at step 204, from the database 104. The selection of procedure the selected patient is to undergo is received from the practitioner at step 206. The details of that procedure, including the navigation data based on pre-operative imaging, may be written, at step 208, to the database 104. The details of the procedure may include a workflow or surgical plan, including a series of steps or directions to begin the surgical procedure, carry out the procedure, and end the procedure. The workflow may include guidance in the form of written instructions or notes that will be presented to the surgeon during the surgery, and/or computer instructions that will be displayed to the surgeon or will be carried out by the robotic surgical tool.

Navigational data for the procedure may include tissue boundaries relevant to the procedure, such as tumor boundaries, vascular and nervous tissue, etc. Navigational data can also include anatomical or fiducial markers, waypoints along the path of a robotic surgical tool 120, and positioning data related to implants such as joint replacements and surgical screws. Pre-surgical planning is well known in robotic surgery and may include several other patient or procedure-specific details. Some or all navigational data points may be assigned a proximity threshold which may be the distance at which the surgeon will begin to receive haptic feedback through the robotic surgical tool 120. For example, in a partial right knee replacement, the surgeon may identify the lateral condyle of the patient's right tibia as navigational data relevant to the procedure. They may identify, based on best practices, manufacturer specifications, and personal preferences, a distance of 1 mm from the surface of the condyle as the proximity threshold for those navigation point(s). In one embodiment, a surgeon may identify the type and level of haptic feedback for a given interaction with a navigation point. For example, a surgeon may indicate a specific level of pushback when the burr meets the bone surface. The surgeon may also indicate the level to which the vibration resulting from the burr-to-bone interaction is transferred to their controls. In one embodiment, a surgeon may indicate navigational points that may need to be avoided. For example, a surgeon performing a partial right knee replacement may indicate point(s) along the popliteus muscle's border as anatomy that needs to be avoided, as damage may compromise knee stability. The surgeon may define a proximity threshold of 5 mm, that when crossed, will trigger pushback against the controls of the robotically surgical tool 120. It is then determined, at step 210, if the practitioner is selecting another patient record from the database 104. If the practitioner is selecting another patient record, the surgical planning module 108 returns to step 202. If the practitioner is not selecting another patient record, the program ends at step 212.

Figure 4:
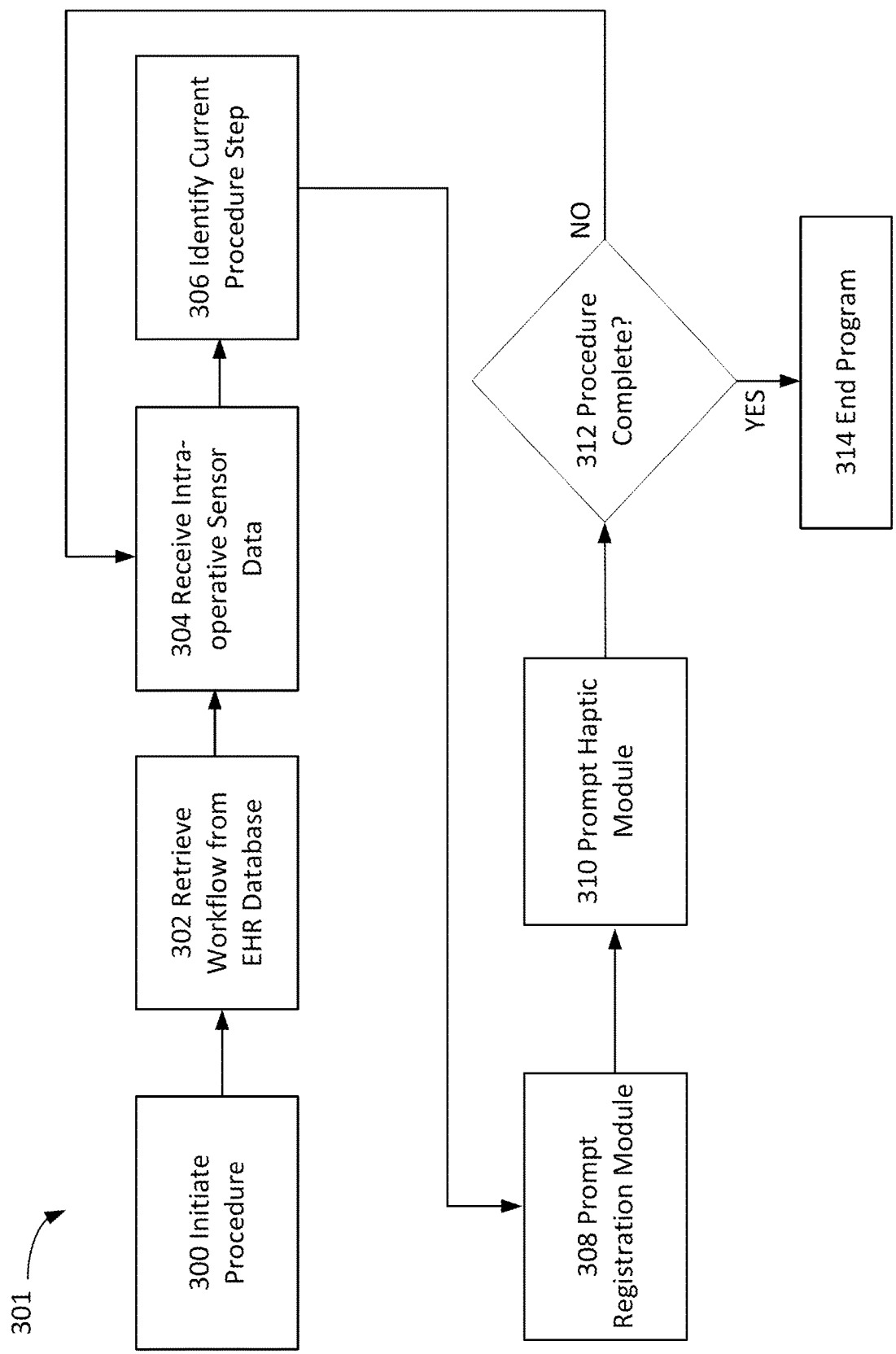
FIG. 4 shows a method for determining a surgical navigation plan and providing haptic feedback during a surgery.

FIG. 4 illustrates an example process utilized by the navigation base module 110. The process begins when the practitioner initiates the procedure, at step 300. The workflow created through the surgical planning module 108 is retrieved, at step 302, from the database 104. Intra-operative data may be received, at step 304, from one or more of the sensors 118. The current step in the procedure workflow may be identified at step 306. In one embodiment, a practitioner may provide input, such as giving a verbal prompt, for a given step in the procedure. Such as "moving to step 3, 3 cm incision above the right knee."

An input device, such as microphone, may receive this prompt, and a processor, such as a natural language or other speech interface, may be used to identify the workflow's corresponding step. In one embodiment, an optical sensor 118 may be used to perform optical recognition connected to a given step in the workflow. Such as recognizing an end effector on a robotic surgical tool 120 is in contact with the lateral condyle of the patient's right tibia may indicate a given step in a partial right knee replacement. In another embodiment, the absolute or relative position of the end effector of the robotic surgical tool 120, or other surgical instruments or supplies present may indicate the step in a procedure's workflow. The registration module 112 may be prompted at step 308. Image registration can be part of any image-guided surgery, such as robotic surgery. Registration integrates different images of the same anatomy into a standard coordinate system. The registration module 112 may return a standard coordinate system based on integrating pre-operative imaging and intra-operative imaging. The haptic module 114 may be prompted at step 310. The haptic module 114 may monitor the robotic surgical tool 120 until a given procedure step is complete. When the step completion is indicated by the haptic module 114, the navigation base module 110 may determine, at step 312, if the procedure is complete. If the procedure is not complete, the process may return to step 304. If the procedure is complete, the process ends at step 314.

Figure 5:
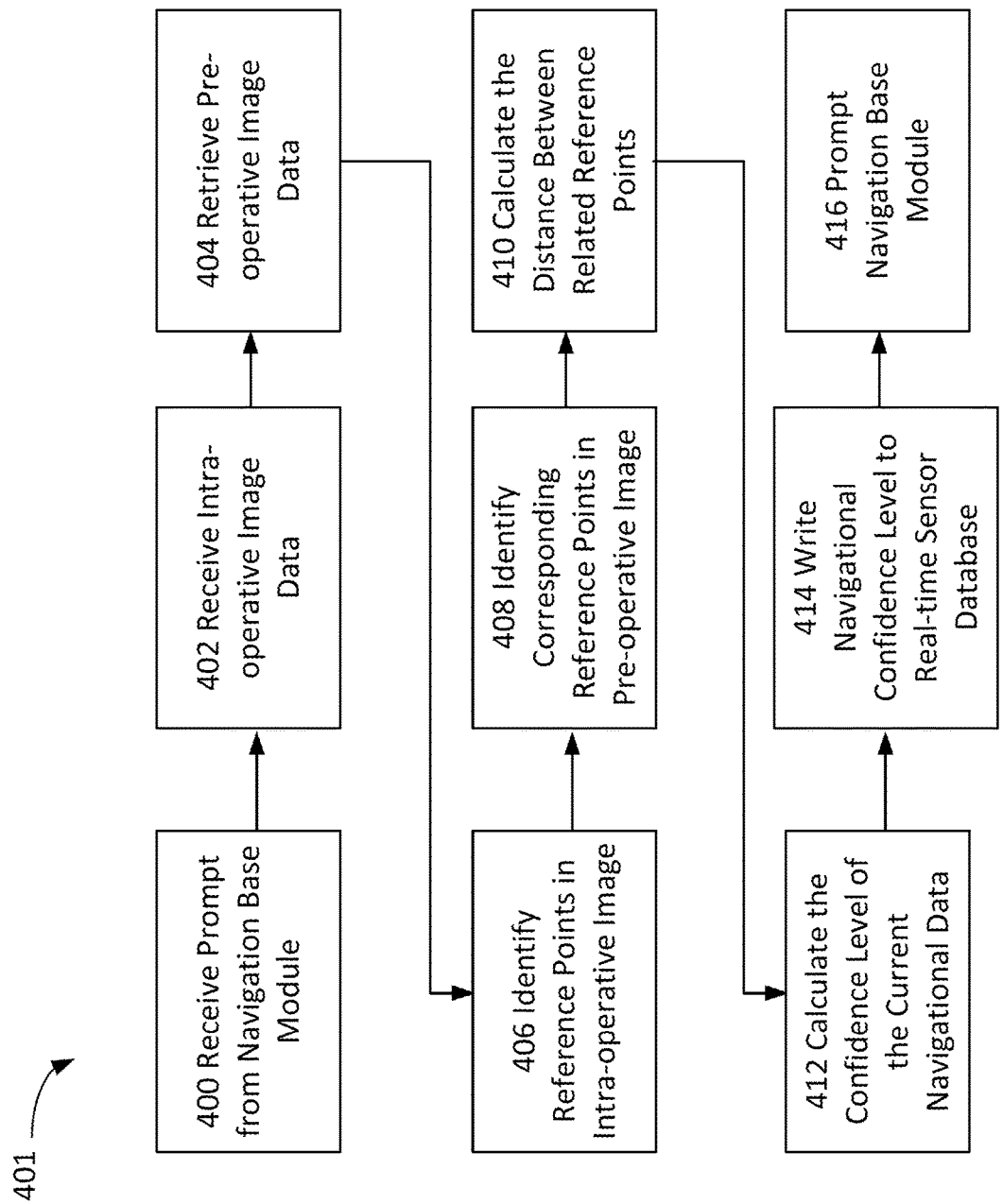
FIG. 5 shows a method of determining a confidence level in a surgical navigation plan during a surgery.

FIG. 5 illustrates an example process 401 to be performed by the registration module 112. The process 401 can begin when a prompt is received, at step 400, from the navigation base module 110. Intra-operative image data is received, at step 402, from one or more of the sensors 118. Pre-operative image data is retrieved, at step 404, from the database 104. Reference points in the intra-operative image may be identified at step 406. Reference points can be identified using any of a variety of techniques such as being identified as salient points looking for specific shapes in an image, being identified as coloration of cells, and/or other appropriate techniques in the medical field for computer analysis. The corresponding reference points may then be identified in the pre-operative image at step 408. The distance between the reference points is calculated at step 410. The distance between the reference points may be calculated using several methods, including homography using stereoscopic cameras and/or determining distances using the standard coordinate system provided by the registration module. For example, stereoscopic cameras can be used to capture intraoperative images, which can be used to determine generate distances in 3D space between the reference points. In the field of computer vision, any two images of the same planar surface in space are related by a homography (assuming a pinhole camera model). This has many practical applications, such as image rectification, image registration, or computation of camera motion-rotation and translation-between two images. Once camera rotation and translation have been extracted from an estimated homography matrix, this information may be used for navigation or to insert models of 3D objects into an image or video to be rendered with the correct perspective and appear to have been part of the original scene.

The distance between the reference points thus determined, the confidence level in the current navigational data, such as the boundary of a tumor removed, is calculated at step 412. The confidence level may be proportional to the distance between the reference points, i.e., the greater the distance between the pre-operative image reference points and the intra-operative image reference points, the lower the confidence level. The confidence interval may be determined by a series of calculated reference points and their respective deviation from the pre-operative estimations and the intra-operative estimations. For example, the mean and standard deviation of the samples is calculated and inputted in the equation $X \pm Z^*(s/\sqrt{n})$, in which X is the mean, Z is the chosen Z-value for the confidence (e.g., a confidence interval of 99% has a Z-value of 2.576), s is the standard deviation, and n is the number of samples. Any of a variety of other techniques may be used to determine confidence intervals, such using correlation functions, like auto correlation and cross correlation functions, and convolution functions.

Additionally and/or alternatively, the confidence level may be based, at least in part, on the width of the confidence interval ($Z^*(s/\sqrt{n})$) relative to the size of the movements needed to complete the operation. The size of the movement that is permitted can be proportional to the confidence interval—meaning a greater confidence interval and permit a greater amount of movement. In one example, the confidence interval may be calculated at ±11 mm, and the movements need to complete the operation are 6 mm. Since the confidence interval exceeds the movements needed to complete the operation, the confidence level may be described as "low," thereby justifying an increased level of haptic feedback to the surgeon to control the instrument's movement with additional resistance. A "low" confidence level can additionally restrict the range of movements that are permitted for the tool. The registered navigational data, including confidence levels, may be written, at step 414, to the real-time sensor database 106. The navigation base module 416 may then be prompted at step 416.

Figure 6A:
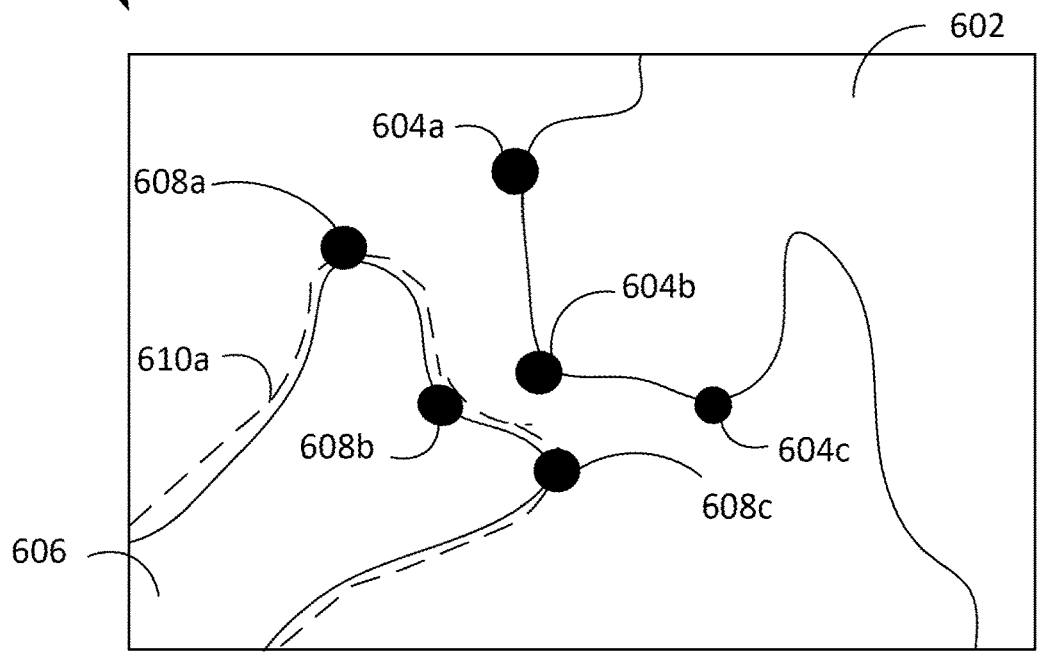
FIG. 6A shows an illustrative example of a pre-surgical image including pre-surgical data.

FIGS. 6A-D illustrate an exemplary comparison of pre-surgical and intra-operative images by the processor registration module and haptic module (described above). FIG. 6A shows an example pre-surgical image 600 including a first anatomical feature 602 and a second anatomical feature 606. As described above, the pre-surgical image 600 can be stored in a database and used in preparing a surgical plan for a procedure including procedure steps, navigation data, and initial surgical thresholds. The first anatomical feature 602 includes first reference points 604a-c, and the second anatomical feature 606 has second reference points 608a-c. The reference points can be added to the image as guides for the surgical plan and navigation data, and may be used to mark the position of relevant aspects of the anatomical feature for use in the procedure and/or for use in positioning the robotic surgical tool during the procedure. Reference points can be added, for example, using structured light, which can be used to detect objects and edges, and can be used to generate a virtual model of the anatomy that is being viewed. In pre-surgical image 600, the second anatomical feature 606 further includes an initial threshold 610a indicating a distance from the second anatomical feature 606 that should be maintained by an end effector of the robotic surgical tool during the procedure. The initial threshold 610a can be predetermined and set by a medical professional based on a review of the pre-surgical image and the procedure to be performed.

Figure 6B:
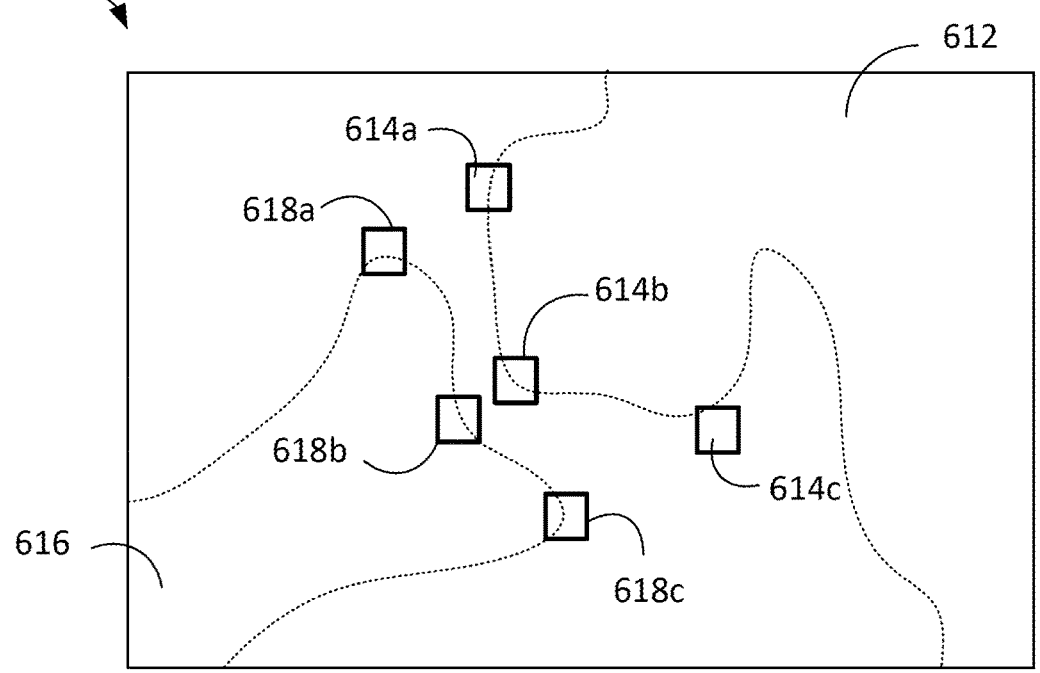
FIG. 6B shows an illustrative example of an intra-operative image including an overlay of reference point markers.

FIG. 6B shows an example real-time image 625 of the anatomical features in the surgical site taken during the procedure, for example by a sensor or camera. The real-time image 625 shows the intra-surgery first anatomical feature 612 and intra-surgery second anatomical feature 616 in the positions that they are in during surgery. In some cases, the positions of the anatomical features of relevance can be altered from their pre-surgery positions by shifting of the patient on the operating table, organ shift, or inaccuracies in pre-surgery imaging. The intra-surgery first reference points 614a-c and intra-surgery second reference points 618a-c can be identified in the real-time image by a processor using image detection.

Figure 6C:
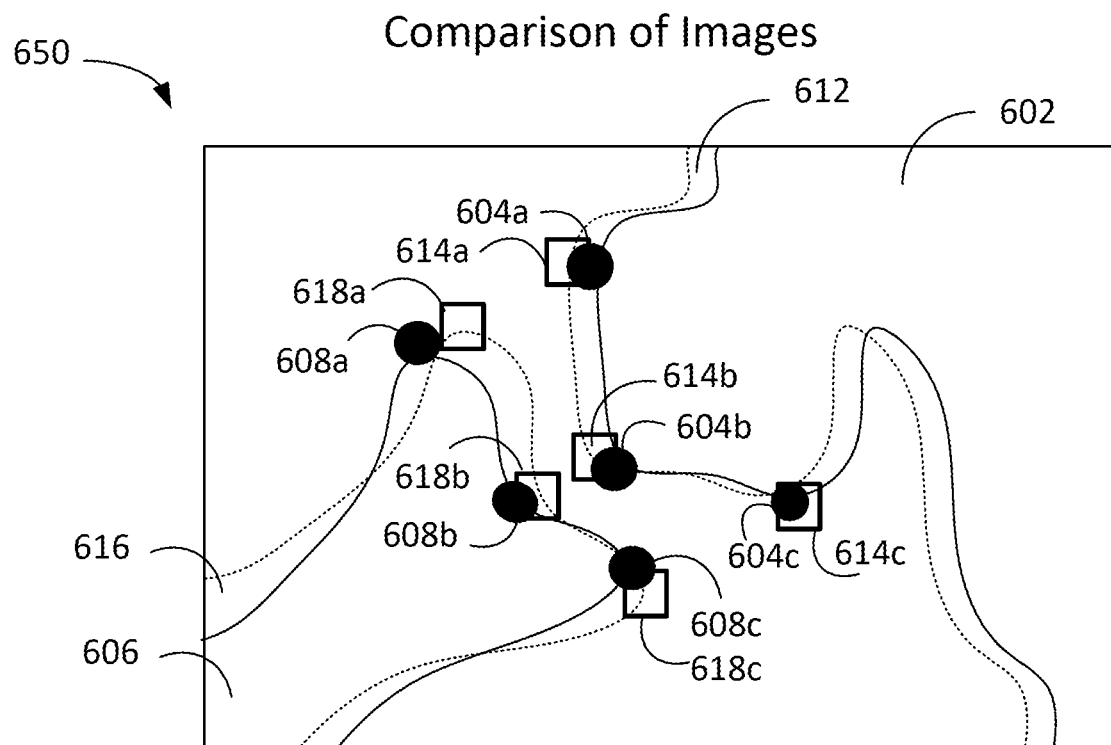
FIG. 6C shows an illustrative example of a comparison of the pre-surgical image of FIG. 6A and the intra-operative image of FIG. 6B.

During the surgical procedure, the real-time image 625 is compared to the pre-surgical image 600 to determine differences between the real-time image 625 and the pre-surgical image 600 on which the surgical plan was based. Depending on the extent of the differences, the surgical plan, including surgical thresholds and navigation data can be adjusted to compensate. FIG. 6C shows an example comparison of the real-time image 625 of FIG. 6B and the pre-surgical image 600 of FIG. 6A. In this example, the images are depicted as being overlaid, though a processor may execute the image comparison through a variety of processes such as pixel-by-pixel comparison or calculation of a cross-correlation in the spatial and frequency domain of the images. The comparison of the images 650 includes the first anatomical feature 602 and intra-surgery first anatomical feature 612 overlaid with first reference points 604a-c and intra-surgery first reference points 614a-c identified to illustrate the differences in the images. The comparison of the images 650 also includes the second anatomical feature 606 and intra-surgery second anatomical feature 616 overlaid with second reference points 608a-c and intra-surgery second reference points 618a-c identified. The processor may calculate distances between the various reference points to determine a shift from the original positions, for example by calculating the distance between second reference point 608a and intra-surgery second reference point 618a to determine a shift in the second anatomical feature 606. In some implementations, the processor calculates the distances between the various first reference points 604a-c and the second reference points 608a-c, and compares these to the distances between the intra-surgery first reference points 614a-c and the intra-surgery second reference points 618a-c to determine a deviation of the positions from the original positions. The processor utilizes the comparison of the images 650 to determine a confidence level in the original surgical plan including navigational data and surgical thresholds. If the comparison of the images 650 indicates that there are significant differences between the pre-surgical image from which the pre-surgical plan was determined and the real-time image of the anatomical features during the procedure, the confidence level can decrease prompting greater caution in following the surgical plan and increasing surgical proximity thresholds.

Figure 6D:
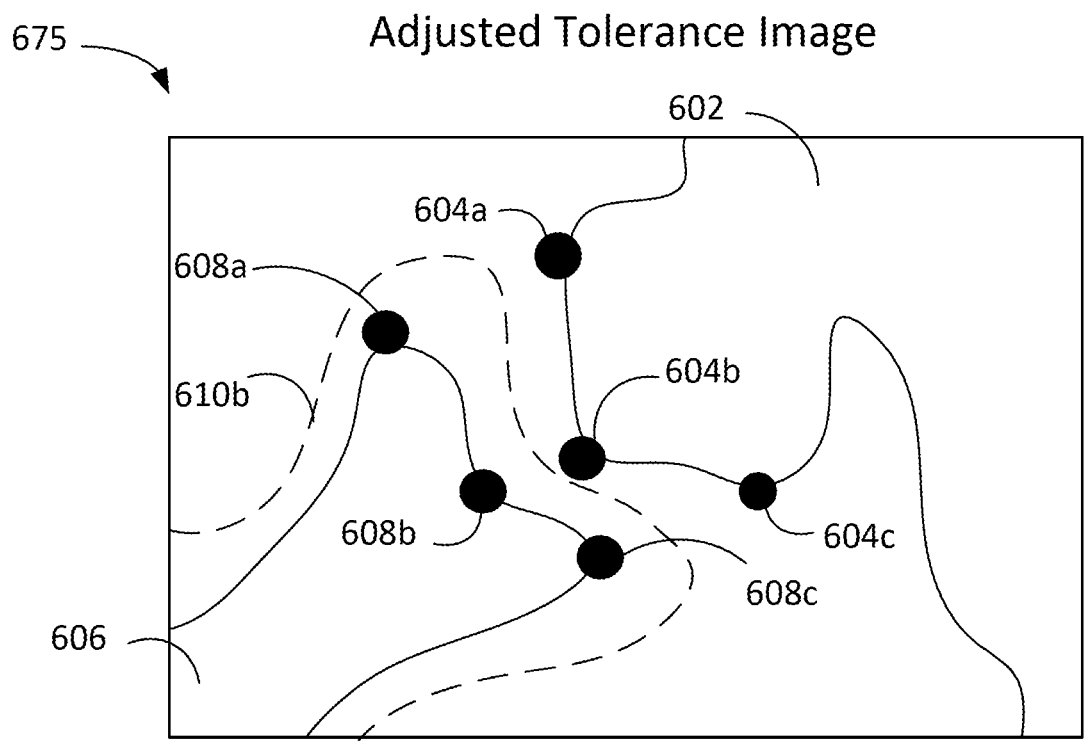
FIG. 6D shows an illustrative example of the pre-surgical image including an updated tolerance level based on the comparison in FIG. 6C.

FIG. 6D shows an example image of an adjusted tolerance and proximity threshold based on the comparison of the images 6C. The processor, after determining differences between the pre-surgical image 6A and the real-time image 6B, calculates the confidence level and adjusts the surgical thresholds based on the confidence level. In FIG. 6D, the first anatomical feature 602 and first reference points 604a-c are identified, and second anatomical feature 606 with second reference points 608a-c are identified. The surgical proximity threshold 610b is altered from the initial surgical threshold 610a, so that a larger threshold is maintained about the second anatomical feature 606. The surgical proximity threshold 610b indicates the perimeter surrounding the second anatomical feature 606 that will prompt haptic feedback if the robotic surgical tool advances within the surgical proximity threshold 610b toward the second anatomical feature 606.

Figure 7:
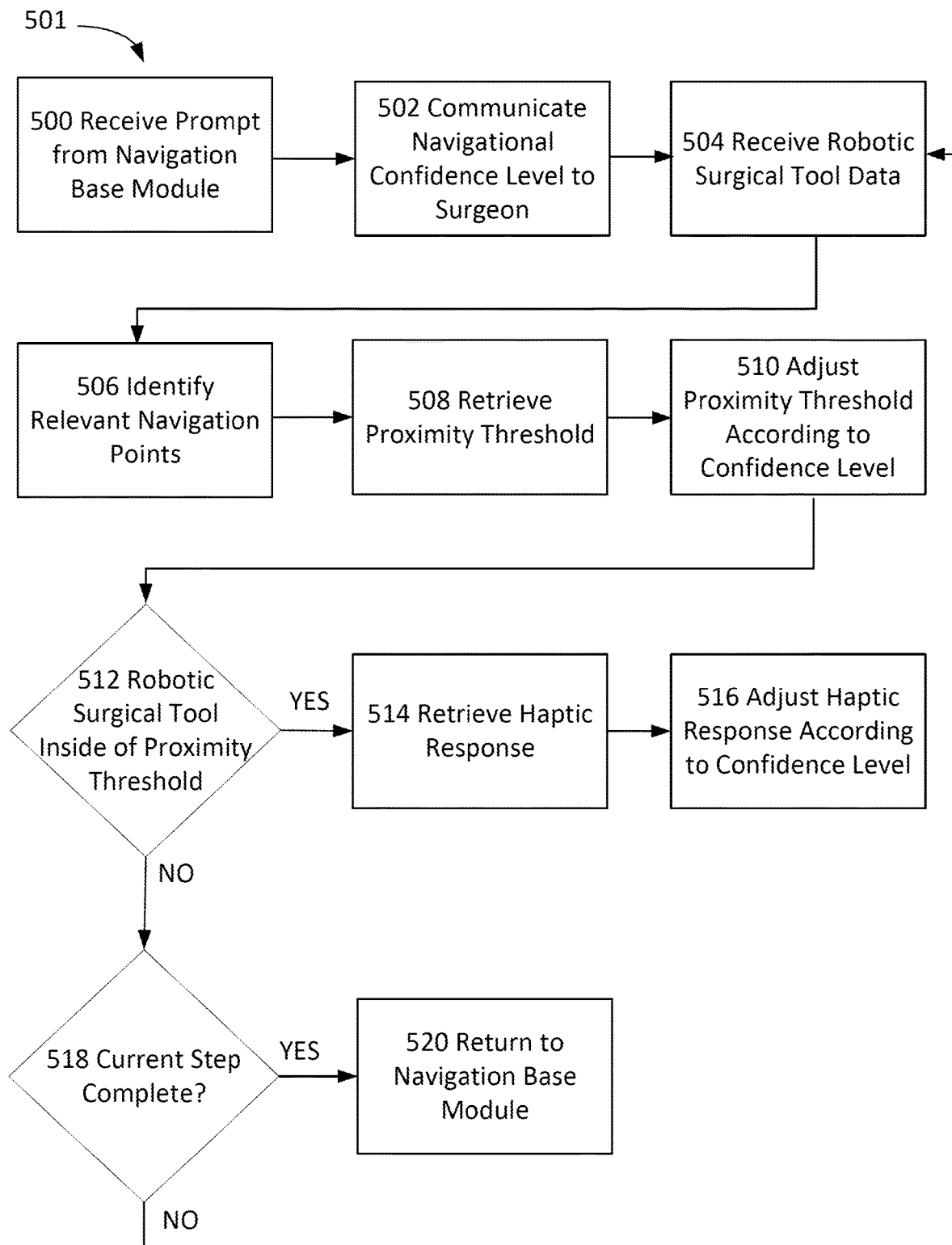
FIG. 7 shows a method of adjusting haptic feedback during a surgery with a robotic surgical tool.

FIG. 7 illustrates an example process 501 utilized by the haptic module 114. The process 501 begins with receiving a prompt, at step 500, from the navigation base module. The haptic module 114 may then communicate at step 502, the confidence level in the surgeon's current navigational data. In one embodiment, a boundary, such as the edge of a tumor, may change in color, brightness, or width based on the confidence level in that boundary or reference point calculated in the registration module 112. For example, color can be used represent the confidence level in a given portion of the navigational data in one embodiment. The confidence level may be communicated to the surgeon through haptic feedback, such as reducing the amount of movement in a robotic surgical tool 120, resulting from a corresponding amount of movement in the controls in proportion to the confidence level. The confidence level can be conveyed to the surgeon in addition to be used to adjust the available movements, such as through haptic feedback and/or audio-visual feedback. For example, an indication that there is a low confidence level can be transmitted to the surgeon through a soft stop/vibration or sound, or it can be a hard stop and have a function that will allow an operator to reassess, override etc. Data related to a robotic surgical tool 120, such as absolute or relative position and movement, end effector status, etc., may be received at step 504. Navigation points relevant to the current context of the procedure are identified at step 506. Which portions of the navigational data are considered relevant may vary based on the surgeon, patient, procedure, robotic surgical tool 120, or their position, condition, or interactions.

In one embodiment, the navigational point, or points nearest the end effector of the robotic surgical tool 120, are the relevant navigation points. For example, as the burr on a robotic surgical tool 120 approaches the lateral condyle of the patient's right tibia during a partial knee replacement, the most relevant navigational point(s) may be the surface of the condyle nearest the burr. In one embodiment, the surface of the condyle may be a first relevant navigational border, and the point(s) to which the implant may be mounted to the tibia may both be identified as they may be part of the same step in the procedure. One or more points on the popliteus muscle may be relevant points the robotic surgical tool 120 may need to avoid in one embodiment.

One or more of the relevant navigational data points may have a proximity threshold associated with it. The proximity threshold may be defined in the surgical planning module 108. The proximity threshold may be retrieved at step 508 from the surgical workflow recorded in the database 104.

The proximity threshold is adjusted, at step 510, based on the confidence level in a given piece of navigational data, as calculated by the registration module 112. In one embodiment, the proximity threshold will increase as the confidence level decreases. For example, the proximity threshold before haptic feedback may be given to the surgeon when the robotic surgical tool 120 approaches the lateral condyle of the right fibula is set to 1 mm. In one embodiment, the pre-operative border's confidence level is 0.61 due to the distance between reference points in the intra-operative image. The 1 mm proximity threshold may be increased to 1.64 mm (1/0.61), resulting in surgeons receiving feedback earlier because of the disparity between pre-operative and intra-operative images. If the confidence level is higher than 0.98, due to minimal disparity between the pre-operative image and the intra-operative image, the 1 mm proximity threshold may be increased to 1.02 mm (1/0.98).

The proximity threshold may be decreased if the intra-operative image is more accurate than the pre-operative image in one embodiment. While pre-operative images are generally higher resolution imaging methods than intra-operative imaging methods due to concerns with time and radiation exposure for both patient and practitioners, there may be circumstances in which the intra-operative image allows the proximity threshold to be decreased. For example, an optical sensor 118, which may be, in some embodiments, a digital camera, integrated with a robotic surgical tool 120 may observe the popliteus muscle boundary's position. This may be a more trusted data source when compared to a pre-operative CT scan, as the intra-operative image may compensate for gravity and other shifting impacts of the patient's current position. The haptic module 114 may then determine, at step 512, if a portion of the robotic surgical tool 120 has crossed a proximity threshold. For example, as the burr approaches the portion of the lateral condyle of the right fibula to be removed, it is determined if it is inside the confidence level adjusted proximity threshold of 1.64 mm. If a portion of the robotic surgical tool 120 crosses a proximity threshold, the type and amplitude of haptic response for crossing that threshold are retrieved, at step 514, from the database 104.

In one embodiment, the surgeon defines the haptic response to a given proximity threshold through the surgical planning module 108. For example, the surgeon may indicate they want vibration of the controls at 30 Hz when they come within 5 mm of the Popliteus muscle. They may want one (1) lb of pushback when they get the burr within one (1) mm of the condyle surface. In one embodiment, the haptic feedback is defined by the manufacturer of the robotic surgical tool 120. The amplitude of the haptic response is adjusted, at step 516, according to the confidence level. In one embodiment, the amplitude of haptic feedback, such as vibration or pushback, may be increased proportionally as the confidence in the navigational data decreases. For example, the surgeon indicated vibration at 30 Hz when the robotic surgical tool 120 came within five (5) mm of the Popliteus muscle. The confidence level in that border is 0.45, as calculated by the registration module 112. The vibration response frequency to crossing the proximity threshold associated with the Popliteus muscle may be increased to 66 Hz (30/0.45). In one embodiment, the confidence level in a given part of the navigational data may be so low to prompt a shutdown of the robotic surgical tool 120.

It is then determined, at step 518, if the current step in the surgical procedure's workflow has been completed. In one embodiment, a practitioner may give a verbal prompt for a given step in the procedure. Such as "moving to step 3, 3 cm incision above the right knee." A microphone may receive this prompt, and a natural language processor may be used to identify the workflow's corresponding step. In one embodiment, an optical sensor 118 may be used to perform optical recognition connected to a given step in the workflow. Such as recognizing an end effector on a robotic surgical tool 120 is in contact with the lateral condyle of the patient's right tibia may indicate a given step in a partial right knee replacement. In another embodiment, the robotic surgical tool 120 is used. Its absolute or relative position, the end effector, being used, or other surgical instruments or supplies present may indicate the step in a procedure's workflow. If the current step is not complete, the haptic module 114 returns to step 504. If the current step is complete, the process returns, at step 520, to the navigation base module 110.

Figure 8:
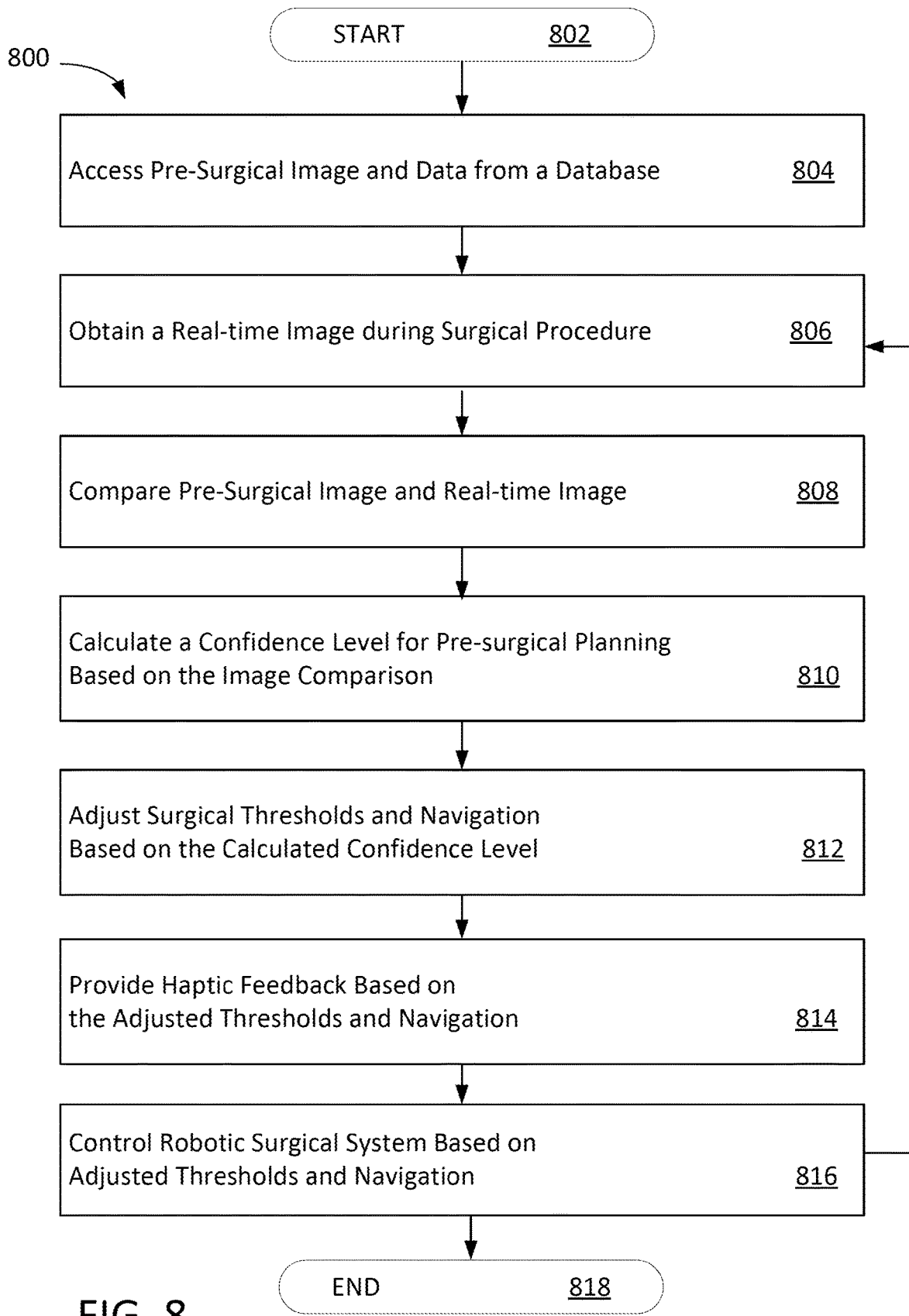
FIG. 8 shows a method of performing a surgical procedure using a robotic surgical system.

FIG. 8 shows an example process 800 for performing a surgical procedure using a robotic surgical system. The process 800 begins at 802 when a medical professional begins a surgical procedure using a robotic surgical system. The medical professional may begin a program on a processor by selecting a patient and a procedure. At step 804, the processor accesses a pre-surgical image and pre-surgical data from a database. The pre-surgical image can be an image of the surgical procedure site obtained at a pre-surgical consultation by invasive or non-invasive methods. The pre-surgical image can include reference points aligned with aspects of anatomical features for use in navigation. The pre-surgical data can include a surgical plan that includes the steps required to perform the procedure as well as guidance for how to control a robotic surgical system to perform the procedure. The pre-surgical data can also include initial proximity thresholds surrounding anatomical features.

At step 806, the processor obtains a real-time image during the surgical procedure of the surgical procedure site. The real-time image can be captured by a sensor or camera in the operating room, worn by a medical professional, or integrated in the end effector of the robotic surgical tool. The processor may add reference points to the real-time image. The processor may filter, orient, or transform the real-time image so that the image can be compared to the pre-surgical image. Any of a variety of image manipulations can be used, such as color, lighting/exposure, contrast, sharpen/blur, edge finding, and/or other image manipulations.

At step 808, the processor compares the pre-surgical image and the real-time image to identify differences between the images. The surgical plan is made based on the pre-surgical image, and changes to the positioning of anatomical features before or during the procedure can require alterations to the surgical plan. The processor can compare the images on a pixel-by-pixel basis, compare groups of pixels to each other, and/or compare shapes generated by a group of pixels, but determining cross-correlation functions between the images, or by comparing the positions of anatomical features or reference points in the images. At step 810, the processor calculates a confidence level for the pre-surgical plan based on the image comparison. The confidence level can be determined by calculation of a confidence interval based on the differences between the images. For example, the confidence level may be proportional to the distance between reference points of the images such that a greater distance between the pre-operative image reference points and the intra-operative image reference points is indicative of a lower confidence level.

At step 812, the processor adjusts surgical thresholds and navigation based on the calculated confidence level. If the confidence level has decreased or is low based on the comparison of the pre-surgical and real-time images, a surgical threshold surrounding an anatomical feature can be increased. In some implementations, the processor prompts the user to approve a change in a surgical threshold based on the confidence level. In some implementations, the processor prompts the user to input a change in a surgical threshold based on the confidence level. In some implementations, the processor displays a changed surgical threshold to the user on a display.

At step 814, haptic feedback is provided based on the adjusted surgical threshold and navigation data. When the robotic surgical tool approaches the anatomical feature and is a distance from the anatomical feature equal to or less than the surgical threshold, haptic feedback will be provided to the user at a haptic interface. The amount or level of haptic feedback can be altered with the confidence level, or with the distance of the robotic surgical tool from the threshold. Haptic feedback can be provided to the medical professional at a control interface such as a joystick or wearable haptic interface.

At step 816, the processor controls the robotic surgical system based on the adjusted thresholds and navigation data. The processor can limit the movement of the robotic surgical system in a particular direction toward an anatomical feature or limit the movement of the system past the surgical threshold. The processor can also instruct the robotic surgical tool to move according to a revised surgical plan. The processor can instruct the robotic surgical tool based on the control instructions of the medical professional user, or can limit the robotic surgical tool's movement independent of the instructions received from the user to prevent advancement beyond a surgical threshold. The process continuously obtains new real-time images during the course of the procedure to continuously update the surgical plan and confidence level in the plan. The thresholds and navigation data can be changed in real-time to account for differences in the pre-surgical image and the images obtained during the procedure. At the end of the procedure, the method ends at 818.

Better surgical outcomes in surgeries using robotic surgical tools can be attained by the methods and devices described herein. By using a sensor that can detect the surgical site during surgery and comparing intra-operative images and other detected parameters to a pre-operative image, the surgical plan and navigation data informing the movements of the robotic surgical tool and prompts to the user can be adapted to account for alterations in the surgical site during surgery, for example due to movement of the patient, organ shift, or inaccuracies in pre-operative imaging. The comparison of the images can be used to determine a confidence level in one or more reference points in the pre-operative image, and haptic responses related to the reference point can be adjusted to reflect the confidence level, alerting the user to the changes in the surgical plan through the haptic feedback as well as through warnings or informative displays.

We claim:

1. A method for performing a surgical procedure using a robotic surgical tool, the method comprising:
   determining, based on a comparison of one or more intra-operative images of an anatomical feature of a patient with one or more pre-operative images of the anatomical feature, a confidence level that indicates a likelihood that a location of the anatomical feature estimated using the one or more intra-operative images is accurate;

setting a boundary around the anatomical feature based on the confidence level;

determining, during the surgical procedure, a current position of the robotic surgical tool relative to at least a portion of the boundary around the anatomical feature; and generating haptic feedback at a haptic interface of a surgeon operating the robotic surgical tool, the haptic feedback adapted to aid the surgeon in maneuvering the robotic surgical tool around the anatomical feature, wherein at least one parameter of the haptic feedback is determined based on the confidence level and the current position of the robotic surgical tool relative to at least a portion of the boundary around the anatomical feature.

2. The method of claim 1, wherein the comparison of the one or more intra-operative images of the anatomical feature of the patient with the one or more pre-operative images of the anatomical feature comprises:

determining a first reference point in the one or more pre-operative images;

detecting a first position of the first reference point in the one or more pre-operative images;

detecting a second position of a corresponding second reference point in the one or more intra-operative image; and determining a distance between the first reference point and the second reference point;

wherein the first reference point and the corresponding second reference point are located at an aspect of the anatomical feature of the patient at or around a surgical site for the surgical procedure.

3. The method of claim 2, wherein determining the confidence level further comprises:

calculating, based on the distance, a confidence interval width; and accessing information indicating a size of movement required by the robotic surgical tool to complete the surgical procedure.

4. The method of claim 1, wherein a predetermined surgical plan for the surgical procedures comprises a workflow including a plurality of steps for completion of the surgical procedure, and wherein the determining the confidence level and setting the boundary around the anatomical feature occurs at least before commencing each of the plurality of steps.

5. The method of claim 4, further comprising adjusting a surgical proximity threshold to define an adjusted boundary for the anatomical feature for one of the plurality of steps of the workflow.

6. The method of claim 1, further comprising:

receiving, from one of a predetermined value or a user input, a first surgical proximity threshold establishing an initial boundary at a first distance around the anatomical feature; and in response to determining the confidence level, updating the first surgical proximity threshold to a second surgical proximity threshold in proportion to the confidence level;

wherein the second surgical proximity threshold establishes an adjusted boundary at a second distance around the first anatomical feature, the first distance being different than the second distance.

7. The method of claim 6, further comprising:

determining that a second position of the robotic surgical tool approaches or passes the adjusted boundary for the anatomical feature;

detecting, at a sensor, the second position of the robotic surgical tool relative to the anatomical feature;

determining that the second position of the robotic surgical tool is within the adjusted boundary established by the second surgical proximity threshold; and generating haptic feedback at a feedback level based on the distance of the second position of the robotic surgical tool from the anatomical feature.

8. The method of claim 7, wherein the sensor is integrated with the robotic surgical tool and is configured to determine a position of the robotic surgical tool relative to a predetermined reference point of the anatomical feature of the patient.

9. A system for performing a surgical procedure using a robotic surgical tool, comprising:

one or more processors; and one or more computer-readable media having instructions stored thereon that, when executed, cause the one or more processors to perform operations comprising:

determining, based on a comparison of one or more intra-operative images of an anatomical feature of a patient with one or more pre-operative images of the anatomical feature, a confidence level that indicates a likelihood that a location of the anatomical feature estimated using the one or more intra-operative images is accurate;

setting a boundary around the anatomical feature based on the confidence level;

determining, during the surgical procedure, a current position of the robotic surgical tool relative to at least a portion of the boundary around the anatomical feature; and generating haptic feedback at a haptic interface of a surgeon operating the robotic surgical tool, the haptic feedback adapted to aid the surgeon in maneuvering the robotic surgical tool around the anatomical feature, wherein at least one parameter of the haptic feedback is determined based on the confidence level and the current position of the robotic surgical tool relative to at least a portion of the boundary around the anatomical feature.

10. The system of claim 9, wherein the comparison of the one or more intra-operative images of the anatomical feature of the patient with the one or more pre-operative images of the anatomical feature is based on actions comprising:

determining a first reference point in the one or more pre-operative images;

detecting a first position of the first reference point in the one or more pre-operative images;

detecting a second position of a corresponding second reference point in the one or more intra-operative image; and determining a distance between the first reference point and the second reference point;

wherein the first reference point and the corresponding second reference point are located at an aspect of the anatomical feature of the patient at or around a surgical site for the surgical procedure.

11. The system of claim 10, wherein determining the confidence level further comprises:

calculating, based on the distance, a confidence interval width; and accessing information indicating a size of movement required by the robotic surgical tool to complete the surgical procedure.

12. The system of claim 9, wherein a predetermined surgical plan for the surgical procedures comprises a workflow including a plurality of steps for completion of the surgical procedure, and wherein the determining the confidence level and setting the boundary around the anatomical feature occurs at least before commencing each of the plurality of steps.

13. The system of claim 12, wherein the operations further comprise adjusting a surgical proximity threshold to define an adjusted boundary for the anatomical feature for one of the plurality of steps of the workflow.

14. The system of claim 9, wherein the operations further comprise:
receiving, from one of a predetermined value or a user input, a first surgical proximity threshold establishing an initial boundary at a first distance around the anatomical feature; and
in response to determining the confidence level, updating the first surgical proximity threshold to a second surgical proximity threshold in proportion to the confidence level;
wherein the second surgical proximity threshold establishes an adjusted boundary at a second distance around the first anatomical feature, the first distance being different than the second distance.

15. The system of claim 14, wherein the operations further comprise:
determining that a second position of the robotic surgical tool approaches or passes the adjusted boundary for the anatomical feature:
detecting, at a sensor, the second position of the robotic surgical tool relative to the anatomical feature;
determining that the second position of the robotic surgical tool is within the adjusted boundary established by the second surgical proximity threshold; and
generating haptic feedback at a feedback level based on the distance of the second position of the robotic surgical tool from the anatomical feature.

16. The system of claim 15, wherein the sensor is integrated with the robotic surgical tool and is configured to determine a position of the robotic surgical tool relative to a predetermined reference point of the anatomical feature of the patient.

17. One or more non-transitory computer-readable media having instructions stored thereon that, when executed by one or more processors, cause the one or more processors to perform operations comprising:
determining, based on a comparison of one or more intra-operative images of an anatomical feature of a patient with one or more pre-operative images of the anatomical feature, a confidence level that indicates a likelihood that a location of the anatomical feature estimated using the one or more intra-operative images is accurate;
setting a boundary around the anatomical feature based on the confidence level;
determining, during the surgical procedure, a current position of the robotic surgical tool relative to at least a portion of the boundary around the anatomical feature; and
generating haptic feedback at a haptic interface of a surgeon operating the robotic surgical tool, the haptic feedback adapted to aid the surgeon in maneuvering the robotic surgical tool around the anatomical feature, wherein at least one parameter of the haptic feedback is determined based on the confidence level and the current position of the robotic surgical tool relative to at least a portion of the boundary around the anatomical feature.

18. The one or more non-transitory computer-readable media of claim 17, wherein the comparison of the one or more intra-operative images of the anatomical feature of the patient with the one or more pre-operative images of the anatomical feature is based on actions comprising:
determining a first reference point in the one or more pre-operative images;
detecting a first position of the first reference point in the one or more pre-operative images;
detecting a second position of a corresponding second reference point in the one or more intra-operative image; and
determining a distance between the first reference point and the second reference point;
wherein the first reference point and the corresponding second reference point are located at an aspect of the anatomical feature of the patient at or around a surgical site for the surgical procedure.

19. The one or more non-transitory computer-readable media of claim 18, wherein determining the confidence level further comprises:
calculating, based on the distance, a confidence interval width; and
accessing information indicating a size of movement required by the robotic surgical tool to complete the surgical procedure.

20. The one or more non-transitory computer-readable media of claim 17, wherein a predetermined surgical plan for the surgical procedures comprises a workflow including a plurality of steps for completion of the surgical procedure, and wherein the determining the confidence level and setting the boundary around the anatomical feature occurs at least before commencing each of the plurality of steps.

* * * * *